US011369069B2

(12) United States Patent
Vanoli

(10) Patent No.: US 11,369,069 B2
(45) Date of Patent: Jun. 28, 2022

(54) LETTUCE VARIETY 'PAYDAY'

(71) Applicant: Pinnacle Seed, Inc., Carmel, CA (US)

(72) Inventor: Mike Vanoli, Carmel, CA (US)

(73) Assignee: Pinnacle Seed, Inc., Carmel, CA (US)

( * ) Notice: Subject to any disclaimer, the term of this patent is extended or adjusted under 35 U.S.C. 154(b) by 0 days.

(21) Appl. No.: 16/996,754

(22) Filed: Aug. 18, 2020

(65) Prior Publication Data

US 2020/0375137 A1 Dec. 3, 2020

Related U.S. Application Data

(62) Division of application No. 16/420,069, filed on May 22, 2019, now Pat. No. 10,785,937.

(60) Provisional application No. 62/675,618, filed on May 23, 2018.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
CPC ................................ A01H 6/1472; A01H 5/12
See application file for complete search history.

(56) References Cited

U.S. PATENT DOCUMENTS

| | | |
|---|---|---|
| 8,362,326 B2 | 1/2013 | Bellec |
| 8,389,810 B2 | 3/2013 | Ammerlaan |
| 8,404,937 B2 | 3/2013 | Gibson |
| 8,476,498 B2 | 7/2013 | Peng |
| 8,772,578 B2 | 7/2014 | Ammerlaan |
| 9,320,250 B2 | 4/2016 | Ammerlaan |
| 9,814,210 B2 | 11/2017 | Ammerlaan et al. |
| 10,123,502 B2 | 11/2018 | Vanoli |
| 10,631,491 B2 | 4/2020 | Vanoli |
| 10,785,937 B1 * | 9/2020 | Vanoli ............... A01H 6/1472 |
| 2012/0278955 A1 | 11/2012 | Gibson |
| 2012/0297496 A1 | 11/2012 | van der Laan |
| 2017/0251622 A1 | 9/2017 | Sinclair et al. |
| 2018/0249669 A1 | 9/2018 | Sinclair |
| 2020/0288660 A1 | 9/2020 | Vanoli |
| 2021/0084853 A1 | 3/2021 | Vanoli |
| 2021/0400893 A1 | 12/2021 | Vanoli |

OTHER PUBLICATIONS

Mikel (Genetic composition of contemporary proprietary U.S. lettuce (*Lactuca sativa* L.) cultivars. Genet Resour Crop Evol 60:89-96 , 2013). (Year: 2013).*
Grant, A. (2018). "Different Lettuce Types: Varieties of Lettuce for the Garden," Obtained from <https://www.gardeningknowhow.com/edible/vegetables/lettuce/different-lettuce-types.htm>, 7 pages.
Liu et al., (1999). "First Report of Tomato Bushy Stunt Virus Isolated from Lettuce," Plant Disease, 83(3):301.
Mikel, M. (2013). "Genetic composition of contemporary proprietary U.S. lettuce (*Lactuca sativa* L.) cultivars," Genet Resour Crop Evol, 60:89-96.
Nagata, R. T. (1992). "Clip and Wash Method of Emasculation for Lettuce." Hortscience 27(8):907-908.
Obermeier et al., (2001). "Characterization of Distinct Tombusviruses that Cause Diseases of Lettuce and Tomato in the Western United States." Phytopathology, 91(8):797-806.
Pinnacle Seed. Jun. 2019. 'Hotshot'. Product Sell Sheet. Available online at Khttp://pinnacleseed.net/sell-sheets/hotshot-sell-sheet.pdf>, Obtained on Sep. 18, 2020.1 page.
Pinnacle Seed. Jun. 2019. 'Uppercut'. Product Sell Sheet. Available online at Khttp://pinnacleseed.net/sell-sheets/PIN-021-Uppercut-sell-sheet-R1-20200310.pdf>, Obtained on Sep. 18, 2020.1 page.
Pinnacle Seed. Oct. 2018. 'Dark Horse'. Product Sell Sheet. Available online at Khttp://pinnacleseed.net/sell-sheets/PIN-021-sell-sheets-dark-horse-R2-20200421.pdf>, Obtained on Sep. 18, 2020.1 page.
Ryder et al., (1974). "Mist depollination of lettuce flowers." Hortscience, 9:584.
US Plant Variety Protection Certificate No. 200700432, dated Mar. 12, 2012, Variety Showtime, Crop Name Lettuce, Applicant Harris Moran Seed Company, 40 pages.
US Plant Variety Protection Certificate No. 201000303, dated Jun. 19, 2013, Variety Caretaker, Crop Name Lettuce, Applicant Harris Moran Seed Company, 28 pages.
US Plant Variety Protection Certificate No. 201100043, dated Mar. 21, 2018, Variety Thunderhead, Crop Name Lettuce, Applicant 3 Star Lettuce, LLC, 34 pages.
US Plant Variety Protection Certificate No. 8900281, dated Jun. 30, 1992, Variety Raider, Crop Name Lettuce, Applicant Genecorp, Inc., 17 pages.
US Plant Variety Protection Certificate No. 9800023, dated Nov. 26, 2020, Variety Headmaster, Crop Name Lettuce, Applicant Progeny Advanced Genetics, Inc., 35 pages.

* cited by examiner

*Primary Examiner* — Bratislav Stankovic
*Assistant Examiner* — Wayne Zhong
(74) *Attorney, Agent, or Firm* — Morrison & Foerster LLP

(57) ABSTRACT

New lettuce variety designated 'Payday' is described. 'Payday' is a lettuce variety exhibiting stability and uniformity.

17 Claims, 53 Drawing Sheets
(53 of 53 Drawing Sheet(s) Filed in Color)

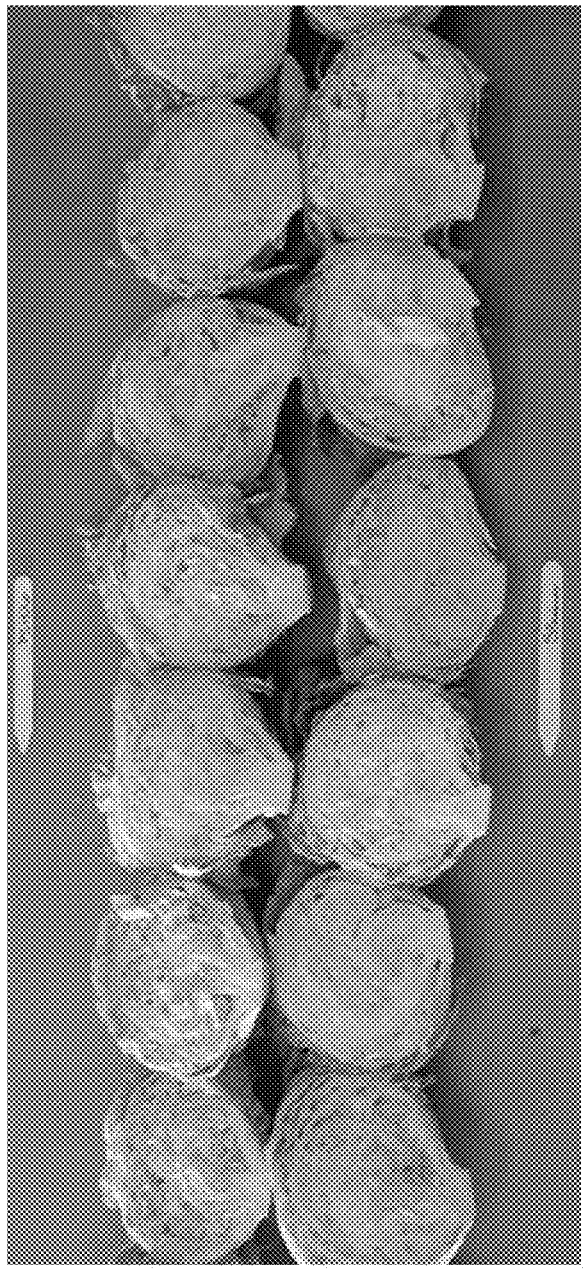
FIG. 2D
FIG. 2E

LETTUCE VARIETY 'PAYDAY'

CROSS-REFERENCE TO RELATED APPLICATION

This application is a divisional of U.S. application Ser. No. 16/420,069, filed May 22, 2019, which claims the benefit of U.S. Provisional Application No. 62/675,618, filed May 23, 2018, which are hereby incorporated by reference in their entirety.

FIELD

This invention relates to the field of plant breeding. In particular, this invention relates to new lettuce, *Lactuca sativa*, varieties 'Sunchaser', 'PS1519', 'Elevate', and 'Payday'.

BACKGROUND

Lettuce is an increasingly popular crop. Worldwide lettuce consumption continues to increase. As a result of this demand, there is a continued need for new lettuce varieties. In particular, there is a need for improved iceberg lettuce varieties that are stable, high yielding, and agronomically sound.

SUMMARY

In order to meet these needs, the present invention is directed to improved lettuce varieties.

In one embodiment, the present invention is directed to lettuce, *Lactuca sativa*, seed designated as 'Sunchaser' having ATCC Accession Number PTA-126633. In one embodiment, the present invention is directed to a *Lactuca sativa* lettuce plant and parts isolated therefrom produced by growing 'Sunchaser' lettuce seed. In another embodiment, the present invention is directed to a *Lactuca sativa* plant and parts isolated therefrom having all the physiological and morphological characteristics of a *Lactuca sativa* plant produced by growing 'Sunchaser' lettuce seed having ATCC Accession Number PTA-126633. In still another embodiment, the present invention is directed to an $F_1$ hybrid *Lactuca sativa* lettuce seed, plants grown from the seed, and a head isolated therefrom having 'Sunchaser' as a parent, where 'Sunchaser' is grown from 'Sunchaser' lettuce seed having ATCC Accession Number PTA-126633.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Sunchaser' lettuce plants. In another embodiment, the present invention is further directed to tissue culture of 'Sunchaser' lettuce plants, and to lettuce plants regenerated from the tissue culture, where the plant has all of the morphological and physiological characteristics of 'Sunchaser' lettuce plants.

The present invention is further directed to a method of selecting lettuce plants by: a) growing more than one 'Sunchaser' lettuce plant, where the plants are grown from lettuce seed having ATCC Accession Number PTA-126633; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Sunchaser' lettuce seed having ATCC Accession Number PTA-126633. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'PS1519'. In one embodiment, the present invention is directed to a *Lactuca sativa* lettuce plant and parts isolated therefrom produced by growing 'PS1519' lettuce seed. In another embodiment, the present invention is directed to a *Lactuca sativa* plant and parts isolated therefrom having all the physiological and morphological characteristics of a *Lactuca sativa* plant produced by growing 'PS1519' lettuce seed. In still another embodiment, the present invention is directed to an $F_1$ hybrid *Lactuca sativa* lettuce seed, plants grown from the seed, and a head isolated therefrom having 'PS1519' as a parent, where 'PS1519' is grown from 'PS1519' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'PS1519' lettuce plants. In another embodiment, the present invention is further directed to tissue culture of 'PS1519' lettuce plants, and to lettuce plants regenerated from the tissue culture, where the plant has all of the morphological and physiological characteristics of 'PS1519' lettuce plants.

The present invention is further directed to a method of selecting lettuce plants by: a) growing more than one 'PS1519' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'PS1519' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Elevate'. In one embodiment, the present invention is directed to a *Lactuca sativa* lettuce plant and parts isolated therefrom produced by growing 'Elevate' lettuce seed. In another embodiment, the present invention is directed to a *Lactuca sativa* plant and parts isolated therefrom having all the physiological and morphological characteristics of a *Lactuca sativa* plant produced by growing 'Elevate' lettuce seed. In still another embodiment, the present invention is directed to an $F_1$ hybrid *Lactuca sativa* lettuce seed, plants grown from the seed, and a head isolated therefrom having 'Elevate' as a parent, where 'Elevate' is grown from 'Elevate' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Elevate' lettuce plants. In another embodiment, the present invention is further directed to tissue culture of 'Elevate' lettuce plants, and to lettuce plants regenerated from the tissue culture, where the plant has all of the morphological and physiological characteristics of 'Elevate' lettuce plants.

The present invention is further directed to a method of selecting lettuce plants by: a) growing more than one 'Elevate' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Elevate' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Payday' having ATCC Accession Number PTA-127190. In one embodiment, the present invention is directed to a *Lactuca sativa* lettuce plant and parts isolated therefrom produced by growing 'Payday' lettuce seed. In another embodiment, the present invention is directed to a *Lactuca sativa* plant and parts isolated therefrom having all the physiological and morphological characteristics of a *Lactuca sativa* plant produced by growing 'Payday' lettuce seed having ATCC Accession Number PTA-127190. In still another embodiment, the present invention is directed to an $F_1$ hybrid *Lactuca sativa* lettuce seed, plants grown from the seed, and a head isolated therefrom having 'Payday' as a parent, where 'Payday' is grown from 'Payday' lettuce seed having ATCC Accession Number PTA-127190.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Payday' lettuce plants. In another embodiment, the present invention is further directed to tissue culture of 'Payday' lettuce plants, and to lettuce plants regenerated from the tissue culture, where the plant has all of the morphological and physiological characteristics of 'Payday' lettuce plants.

The present invention is further directed to a method of selecting lettuce plants by: a) growing more than one 'Payday' lettuce plant, where the plants are grown from lettuce seed having ATCC Accession Number PTA-127190; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Payday' lettuce seed having ATCC Accession Number PTA-127190. In still another embodiment, the present invention is further directed to lettuce plants, lettuce parts from the lettuce plants (e.g., lettuce heads), and seeds produced therefrom where the lettuce plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows heads of lettuce variety 'Sunchaser' (PS1516). FIG. 1B shows a side view of heads of lettuce variety 'Sunchaser'. FIG. 1C shows a bottom view of heads of lettuce variety 'Sunchaser'. FIG. 1D shows a cross-sectional view of heads of lettuce variety 'Sunchaser'. FIG. 1E shows a seedling of lettuce variety 'Sunchaser'. FIG. 1F shows a seedling of lettuce variety 'Sunchaser' (PS1516). FIG. 1G shows plants of lettuce variety 'Sunchaser'. FIG. 1H shows a bottom view of heads of lettuce variety 'Sunchaser' (PS1516). FIG. 1I shows bolting plants of lettuce variety 'Sunchaser'.

FIGS. 2A-2K show comparisons between lettuce varieties 'Sunchaser' (PS1516), 'Speedway' (PS1169; U.S. Pat. No. 8,404,937). FIG. 2A shows heads of lettuce varieties 'Speedway' (on left) and 'Sunchaser' (PS1516; on right). FIG. 2B shows a side view of heads of lettuce varieties 'Sunchaser' (PS1516; top row) and 'Speedway' (bottom row). FIG. 2C shows a bottom view of heads of lettuce varieties 'Sunchaser' (PS1516; top row) and 'Speedway' (bottom row). FIG. 2D shows a cross-sectional view of heads of lettuce varieties 'Sunchaser' (PS1516; top row) and 'Speedway' (bottom row). FIG. 2E shows a top view of heads of lettuce varieties 'Sunchaser' (PS1516; top row) and 'Speedway' (bottom row). FIG. 2F shows seedlings of lettuce varieties 'Sunchaser' (PS1516; bottom row) and 'Speedway' (PS1169; top row). FIG. 2G shows a seedling of lettuce variety 'Speedway' (PS1169). FIG. 2H shows a seedling of lettuce variety 'Speedway'. FIG. 2I shows plants of lettuce variety 'Speedway'. FIG. 2J shows a bottom view of heads of lettuce variety 'Speedway'. FIG. 2K shows bolting plants of lettuce variety 'Speedway'.

FIG. 3A shows heads of lettuce variety 'PS1519' (14RDSJV022-3). FIG. 3B shows a side view of a head of lettuce variety 'PS1519' (14RDSJV022-3). FIG. 3C shows a bottom view of a head of lettuce variety 'PS1519' (14RDSJV022-3). FIG. 3D shows a cross-sectional view of a head of lettuce variety 'PS1519' (14RDSJV022-3). FIG. 3E shows heads of lettuce variety 'PS1519'. FIG. 3F shows plants of lettuce variety 'PS1519'. FIG. 3G shows plants of lettuce variety 'PS1519'. FIG. 3H shows bottom and cross-sectional views of heads of lettuce variety 'PS1519' (14RDSJV022-3). FIG. 3I shows a seedling of lettuce variety 'PS1519'. FIG. 3J shows bolting plants of lettuce variety 'PS1519' (14RDSJV022-3).

FIG. 4A shows heads of lettuce varieties 'Raider' (PS1014; on left) and 'PS1519' (14RDSJV022-3; on right). FIG. 4P shows bolting plants of lettuce variety 'Raider.'

FIG. 5A shows heads of lettuce variety 'Elevate' (PS1512). FIG. 5B shows a top view of a head of lettuce variety 'Elevate' (PS1512). FIG. 5C shows a bottom view of a head of lettuce variety 'Elevate' (PS1512). FIG. 5D shows a cross-sectional view of a head of lettuce variety 'Elevate'. FIG. 5E shows plants of lettuce variety 'Elevate' (PS1512). FIG. 5F shows heads of lettuce variety 'Elevate'. FIG. 5G shows a seedling of lettuce variety 'Elevate' (PS1512). FIG. 5H shows a bottom view of a head of lettuce variety 'Elevate'. FIG. 5I shows a bottom view of a head of lettuce variety 'Elevate'. FIG. 5J shows cross-sectional views of a head of lettuce variety 'Elevate'. FIG. 5K shows cross-sectional views of a head of lettuce variety 'Elevate'. FIG. 5L shows heads of lettuce variety 'Elevate' in a carton. FIG. 5M shows bolting plants of lettuce variety 'Elevate'.

FIG. 6A shows heads of lettuce varieties 'Elevate' (PS1512; on left) and 'Gun Slinger' (PS1013; on right). FIG. 6P shows bolting plants of lettuce variety 'Gun Slinger'.

FIGS. 7A-7J show lettuce variety 'Payday' (PS1515). FIG. 7A shows heads of lettuce variety 'Payday' (PS1515). FIG. 7B shows a side view of heads of lettuce variety 'Payday' (PS1515). FIG. 7C shows a bottom view of heads of lettuce variety 'Payday' (PS1515). FIG. 7D shows a cross-sectional view of heads of lettuce variety 'Payday' (PS1515). FIG. 7E shows plants of lettuce variety 'Payday'. FIG. 7F shows heads of lettuce variety 'Payday' (PS1515). FIG. 7G shows a seedling of lettuce variety 'Payday'. FIG. 7H shows a seedling of lettuce variety 'Payday' (PS1515). FIG. 7I shows bottom views of heads of lettuce variety 'Payday' (PS1515). FIG. 7J shows bolting plants of lettuce variety 'Payday' (PS1515).

FIG. 8A shows heads of lettuce varieties 'Primetime' (PS1037; on left) and 'Payday' (PS1515; on right). FIG. 8B shows side views of heads of lettuce varieties 'Payday' (PS1515; top row) and 'Primetime' (PS1037; bottom row). FIG. 8C shows bottom views of heads of lettuce varieties 'Payday' (PS1515; top row) and 'Primetime' (PS1037; bottom row). FIG. 8D shows cross-sectional views of heads of lettuce varieties 'Payday' (PS1515; top row) and 'Primetime' (PS1037; bottom row). FIG. 8E shows top views of heads of lettuce varieties 'Payday' (PS1515; top row) and 'Primetime' (PS1037; bottom row). FIG. 8F shows seedlings of lettuce varieties 'Payday' (PS1515; bottom row) and 'Primetime' (PS1037; top row). FIG. 8G shows a seedling of lettuce variety 'Primetime'. FIG. 8H shows a seedling of lettuce variety 'Primetime' (PS1037). FIG. 8I shows leaves of lettuce varieties 'Payday' (PS1515; two on right) and 'Primetime' (PS1037; two on left). FIG. 8J shows bottom views of heads of lettuce variety 'Primetime' (PS1037). FIG. 8K shows plants of lettuce variety 'Primetime' (PS1037). FIG. 8L shows heads of lettuce variety 'Primetime' (PS1037). FIG. 8M shows bolting plants of lettuce variety 'Primetime'.

DETAILED DESCRIPTION

Definitions

Figure 1A:
FIGS. 1A-1I show lettuce variety 'Sunchaser' (PS1516).
Figure 1B:
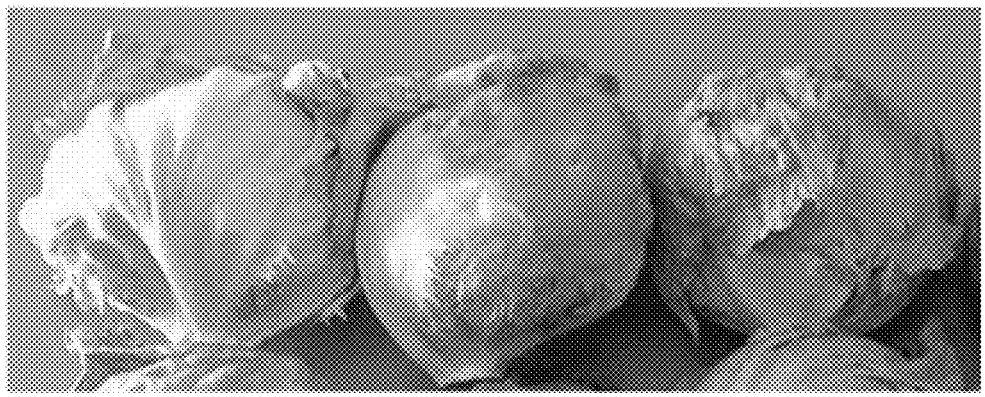
Figure 1C:
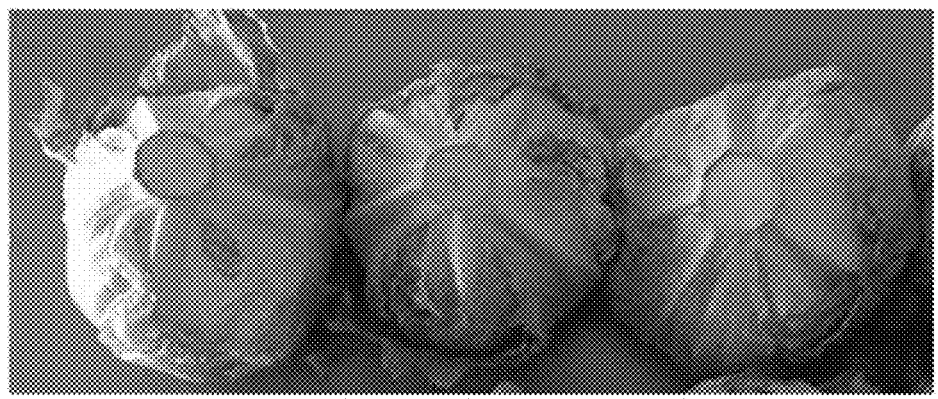
Figure 1D:
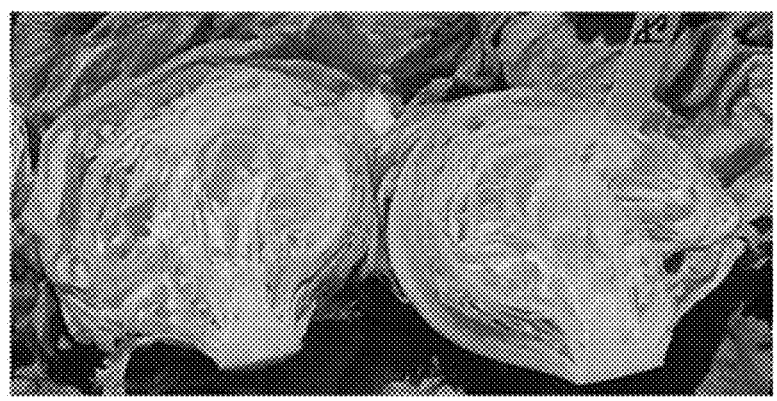

In order to more clearly understand the invention, the following definitions are provided:

Core Length: Core length is the length of the internal lettuce stem. Core length is measured from the base of the cut head to the tip of the core.

Core Diameter: Core diameter is the diameter of the lettuce stem at the base of the cut head.

Heart Length: Heart length is the length of the vertically sliced lettuce plant as measured from the base of the cut stem to the top leaf margin of the longest outermost leaf that encloses the green leaf heart.

Plant Diameter: The plant diameter is a measurement across the top of the lettuce plant at its widest point. The measurement of frame diameter is taken from the outer most leaf tip horizontally to the outer most leaf tip.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Head Weight: Head weight is the weight of the marketable lettuce plant, cut and trimmed to market specifications.

Lettuce Mosaic Virus: A disease that can cause a stunted, deformed, or mottled pattern in young lettuce and yellow, twisted, and deformed leaves in older lettuce.

Maturity Date: Maturity refers to the stage when the plants are of full size or optimum weight, in marketable form or shape to be of commercial or economic value.

Munsell: Munsell refers to the Munsell Color Chart, which uses the Munsell color system.

*Nasonovia ribisnigri*: A lettuce aphid that colonizes the innermost leaves of the lettuce plant, contaminating areas that cannot be treated easily with insecticides.

Tip burn: Means a browning of the edges or tips of lettuce leaves that is a physiological response to a lack of calcium.

Tomato Bushy Stunt: Lettuce dieback was first observed in California in the mid-1980s, and reports of the disease have increased over the last 10 years. Complete crop losses have occurred in fields of Green Leaf lettuce, and no commercial Green Leaf cultivar has been shown to be resistant to the disease. In the U.S., Green Leaf is a rapidly growing market segment, having increased 68% over the last five years (USDA, 2002). The disease has occurred in commercial fields of some leaf lettuce cultivars; however, symptoms have never been observed on any modern crisphead (iceberg) cultivars. Lettuce dieback is caused by several related tombusviruses including tomato bushy stunt virus (TBSV) and lettuce necrotic stunt virus (LNSV) (Liu et al., 1999; Obermeier et al., 2001). These are soil-borne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Resistance to Tomato Busy Stunt refers to a level of resistance in a lettuce variety as measured by visual symptoms. Resistance is deemed present when symptoms are not present in at least 95% of a lettuce variety when exposed to tomato bushy stunt virus (TBSV).

Taking into account these definitions, the present invention is directed to seeds of the lettuce varieties 'Sunchaser', 'PS1519', 'Elevate', and 'Payday', plants produced by growing 'Sunchaser', 'PS1519', 'Elevate', and/or 'Payday' lettuce seeds, heads isolated or harvested from the plants, one or more plants selected from a collection of 'Sunchaser', 'PS1519', 'Elevate', and/or 'Payday' plants and seeds derived or produced therefrom; plants produced by crossing a lettuce plant with a 'Sunchaser', 'PS1519', 'Elevate', and/or 'Payday' lettuce plant and seeds derived or produced therefrom.

Objective Description of the Variety 'Sunchaser'

Figure 1E:
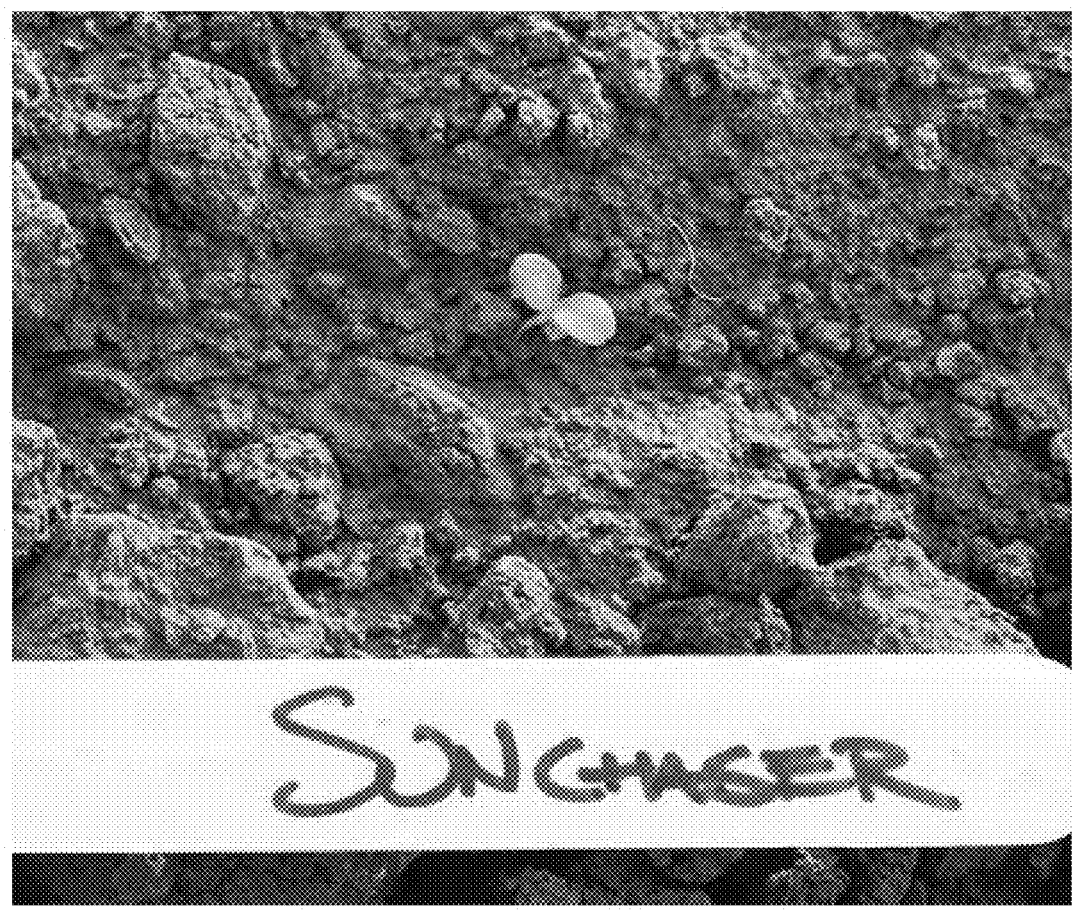
Figure 1F:
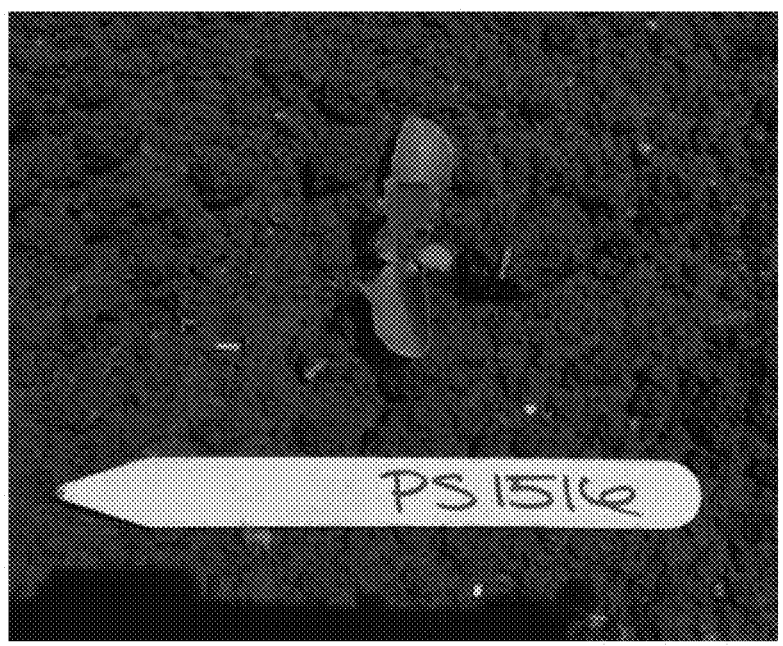
Figure 1G:
Figure 1H:
Figure 1I:
Figure 2A:
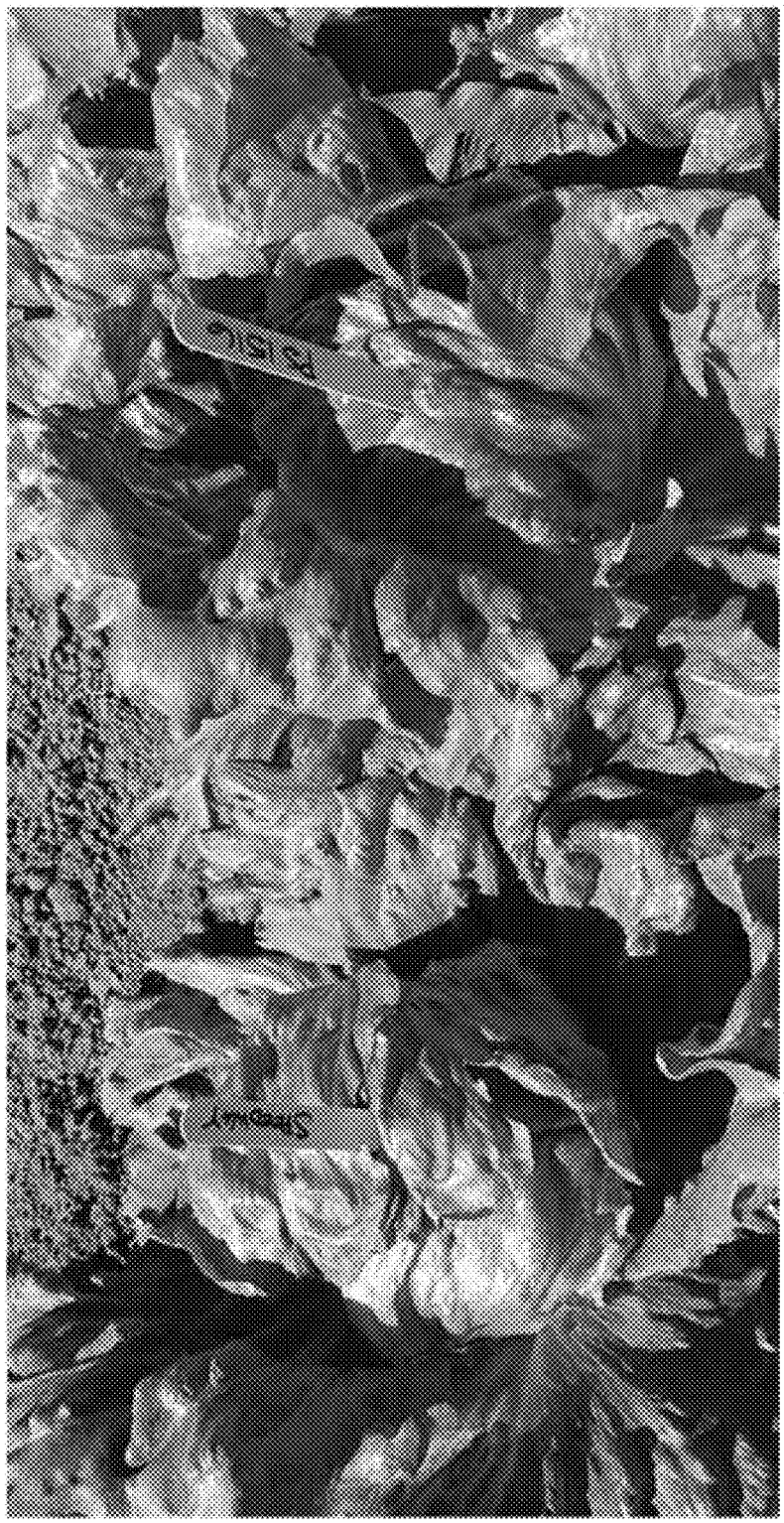
Figure 2B:
Figure 2C:
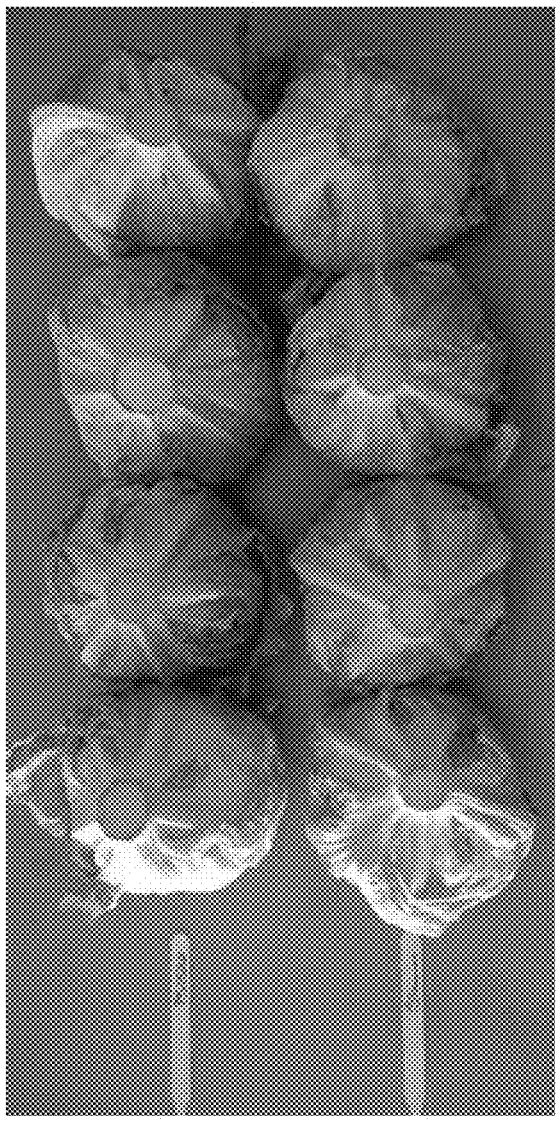
Figure 2F:
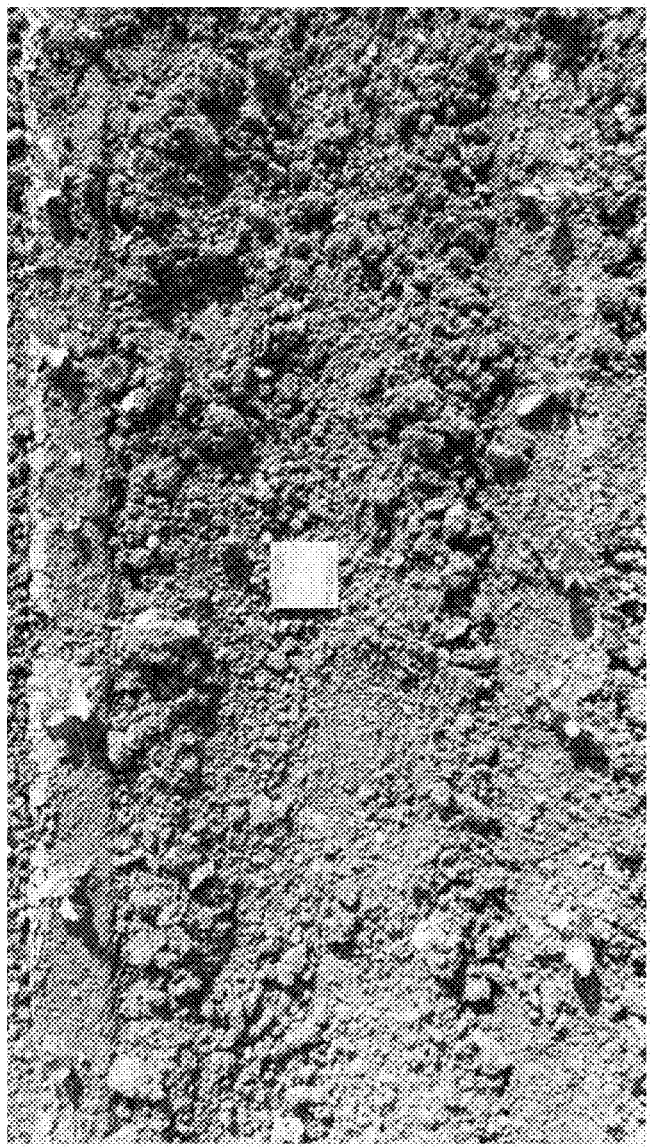
Figure 2H:
Figure 2G:
Figure 2I:
Figure 2J:
Figure 2K:

'Sunchaser' is an open-pollinated iceberg lettuce variety. This variety is distinct and unique to all other iceberg lettuce varieties due to its later maturing time, larger core diameter, larger stem length, increased head weight, more upright frame, and more upright heading. Moreover, 'Sunchaser' has a growing season that includes autumn, and is suitable for cultivation in the open. 'Sunchaser' is adapted to growing in regions such as the Southwest regions of the United States, for example California and the Arizona desert. FIGS. 1A-1D and 1H depict heads of lettuce variety 'Sunchaser', FIGS. 1E-1F depict seedlings of lettuce variety 'Sunchaser', FIG. 1G depicts plants of lettuce variety 'Sunchaser', and FIG. 1I depicts bolting plants of lettuce variety 'Sunchaser'. Lettuce variety 'Sunchaser' is the result of numerous generations of plant selections chosen for its later maturing time, more upright frame, more upright heading, and increased head weight.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Sunchaser'.

Lettuce variety 'Sunchaser' has the following morphologic and other characteristics:
Plant type: Crisp (i.e., iceberg); Vanguard Group
Seed:
Color: White
Leaves:
Cotyledon to fourth leaf stage:
    Shape of cotyledons: Intermediate
    Shape of fourth leaf: Oval
    Apical margin: Finely dentate
    Basal margin: Moderately dentate
    Undulation: Slight
    Green color: Dark green
    Anthocyanin:
        Distribution: Absent
        Cupping: Slight
        Reflexing: None
Mature leaves:
    Incision depth of margin: Moderate (comparable to 'Vanguard')
    Indentation of margin: Crenate (comparable to 'Vanguard')
    Undulations of the apical margin: Moderate (comparable to 'Vanguard')
    Green color: Munsell 5GY 5/6 (Dark green; comparable to 'Vanguard')
    Hue of green color of mature outer leaves: Greyish
    Intensity of color of mature outer leaves: Medium
    Anthocyanin:
        Coloration: Absent
        Distribution: Absent
        Size: Medium
        Glossiness: Dull (comparable to 'Vanguard')
        Blistering: Moderate (comparable to 'Vanguard')
        Leaf thickness: Thick
        Trichomes: Absent (smooth)
Plant:
Spread of frame leaves: 49.8 cm
Head diameter: 139.1 mm
Head shape: Elongate
Head degree of overlapping of upper part of leaves: Strong
Head size class: Medium
Head per carton: 24
Head weight: 647.7 g
Head firmness: Firm
Plant Butt:
Shape: Rounded
Midrib: Moderately raised
Plant Core:
Diameter at base of head: 34.6 mm
Ratio of head diameter/core diameter: 4.0
Core height from base of head to apex: 30.2 mm
Bolting:
Class: Medium
Bolter leaves: Curved
Margin: Entire
Color: Dark green
Days from first water date to seed stalk emergence under summer conditions: 71 days
Bolter Habit:
Lateral shoots: Present
Basal side shoots: Absent
Disease/Pest Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible Pests:

*Nasonovia ribisnigri* biotype 0 (Nr:0): Susceptible

Comparisons to Other Lettuce Variety

Table 1 below compares characteristics of lettuce variety 'Sunchaser' with the lettuce variety 'Speedway' (U.S. Pat. No. 8,404,937). Column 1 lists the characteristics, column 2 shows the characteristics for lettuce variety 'Sunchaser', and column 3 shows the characteristics for lettuce variety 'Speedway'.

TABLE 1

| Characteristic | 'Sunchaser' | 'Speedway' |
|---|---|---|
| Time to maturity | Later maturing | Earlier maturing |
| Core diameter | Larger core diameter | Smaller core diameter |
| Stem length | Larger stem length | Smaller stem length |
| Frame | More upright frame | Less upright frame |
| Heading | More upright heading | Less upright heading |
| Head weight | Increased head weight | Lower head weight |

Table 2 below compares additional characteristics of lettuce variety 'Sunchaser' with the lettuce variety 'Speedway'. Column 1 lists the characteristics, column 2 shows the characteristics for lettuce variety 'Sunchaser', and column 3 shows the characteristics for lettuce variety 'Speedway'.

TABLE 2

| Characteristic | 'Sunchaser' | 'Speedway' |
|---|---|---|
| Green color of mature leaves | Munsell 5GY 5/6 | Munsell 5GY 4/8 |
| Spread of frame leaves | 49.8 cm | 50.08 cm |
| Head diameter | 139.1 mm | 141.9 mm |
| Head weight | 647.7 g | 599.7 g |
| Diameter at base of head | 34.6 mm | 31.35 mm |
| Core height from base to apex | 30.2 mm | 26.9 mm |

Tables 3A and 3B below show results of a first trial that compares the head weight, head diameter, core length, core diameter, and frame diameter of 20 plants of the lettuce variety 'Sunchaser' (Table 3A) with those of 20 plants of lettuce variety 'Speedway' (Table 3B).

TABLE 3A

| 'Sunchaser' | Head Wt. | Head Diameter | Core Length | Core Diameter | Frame Diameter |
|---|---|---|---|---|---|
| Max | 685 g | 157 mm | 45 mm | 34 mm | 51.4 cm |
| Min | 300 g | 122 mm | 24 mm | 26 mm | 43.7 cm |
| Average | 484.75 g | 142.30 mm | 33.00 mm | 29.80 mm | 47.43 cm |
| Std. Dev | 106.05 | 10.48 | 6.40 | 2.31 | 2.53 cm |

TABLE 3B

| 'Speedway' | Head Wt. | Head Diameter | Core Length | Core Diameter | Frame Diameter |
|---|---|---|---|---|---|
| Max | 565 g | 167 mm | 35 mm | 31 mm | 52.4 cm |
| Min | 335 g | 123 mm | 21 mm | 26 mm | 44.5 cm |
| Average | 456.00 g | 143.30 mm | 26.70 mm | 28.45 mm | 48.03 cm |
| Std. Dev | 72.40 | 11.11 | 4.00 | 1.54 | 2.48 |

Tables 4A and 4B below show results of a second trial that compares the head weight, head diameter, core length, core diameter, and frame diameter of 20 plants of the lettuce variety 'Sunchaser' (Table 4A) with those of 20 plants of lettuce variety 'Speedway' (Table 4B).

TABLE 4A

| 'Sunchaser' | Head Wt. | Head Diameter | Core Length | Core Diameter | Frame Diameter |
|---|---|---|---|---|---|
| Max | 680 g | 138 mm | 32 mm | 37 mm | 50 cm |
| Min | 395 g | 113 mm | 21 mm | 31 mm | 44 cm |
| Average | 522 g | 125.65 mm | 25.8 mm | 33.55 mm | 46.6 cm |
| Std. Dev | 75.47 | 7.56 | 2.65 | 1.61 | 1.73 |

TABLE 4B

| 'Speedway' | Head Wt. | Head Diameter | Core Length | Core Diameter | Frame Diameter |
|---|---|---|---|---|---|
| Max | 700 g | 147 mm | 27 mm | 34 mm | 51 cm |
| Min | 435 g | 118 mm | 20 mm | 27 mm | 43 cm |
| Average | 563.75 g | 134 mm | 23.65 mm | 31.5 mm | 47.5 cm |
| Std. Dev | 77.08 | 9.16 | 1.81 | 1.99 | 2.19 |

Tables 5A and 5B below show results of a third trial that compares the head weight, head diameter, core length, core diameter, and frame diameter of 20 plants of the lettuce variety 'Sunchaser' (Table 5A) with those of 20 plants of lettuce variety 'Speedway' (Table 5B).

TABLE 5A

| 'Sunchaser' | Head Wt. | Head Diameter | Core Length | Core Diameter | Frame Diameter |
|---|---|---|---|---|---|
| Max | 1270 g | 171 mm | 40 mm | 49 mm | 61 cm |
| Min | 730 g | 125 mm | 20 mm | 35 mm | 48 cm |
| Average | 935.5 g | 149.2 mm | 31.85 mm | 40.5 mm | 55.5 cm |
| Std. Dev | 149.15 | 11.39 | 4.86 | 3.25 | 2.96 |

TABLE 5B

| 'Speedway' | Head Wt. | Head Diameter | Core Length | Core Diameter | Frame Diameter |
|---|---|---|---|---|---|
| Max | 1010 g | 170 mm | 40 mm | 40 mm | 60 cm |
| Min | 580 g | 122 mm | 19 mm | 31 mm | 48 cm |
| Average | 779.25 g | 148.35 mm | 30.5 mm | 34.1 mm | 54.7 cm |
| Std. Dev | 118.93 | 12.39 | 4.50 | 2.71 | 3.01 |

Further distinguishing features are apparent from the comparison of the two varieties depicted in FIGS. 2A-2K.

Objective Description of the Variety 'PS1519'

Figure 3A:
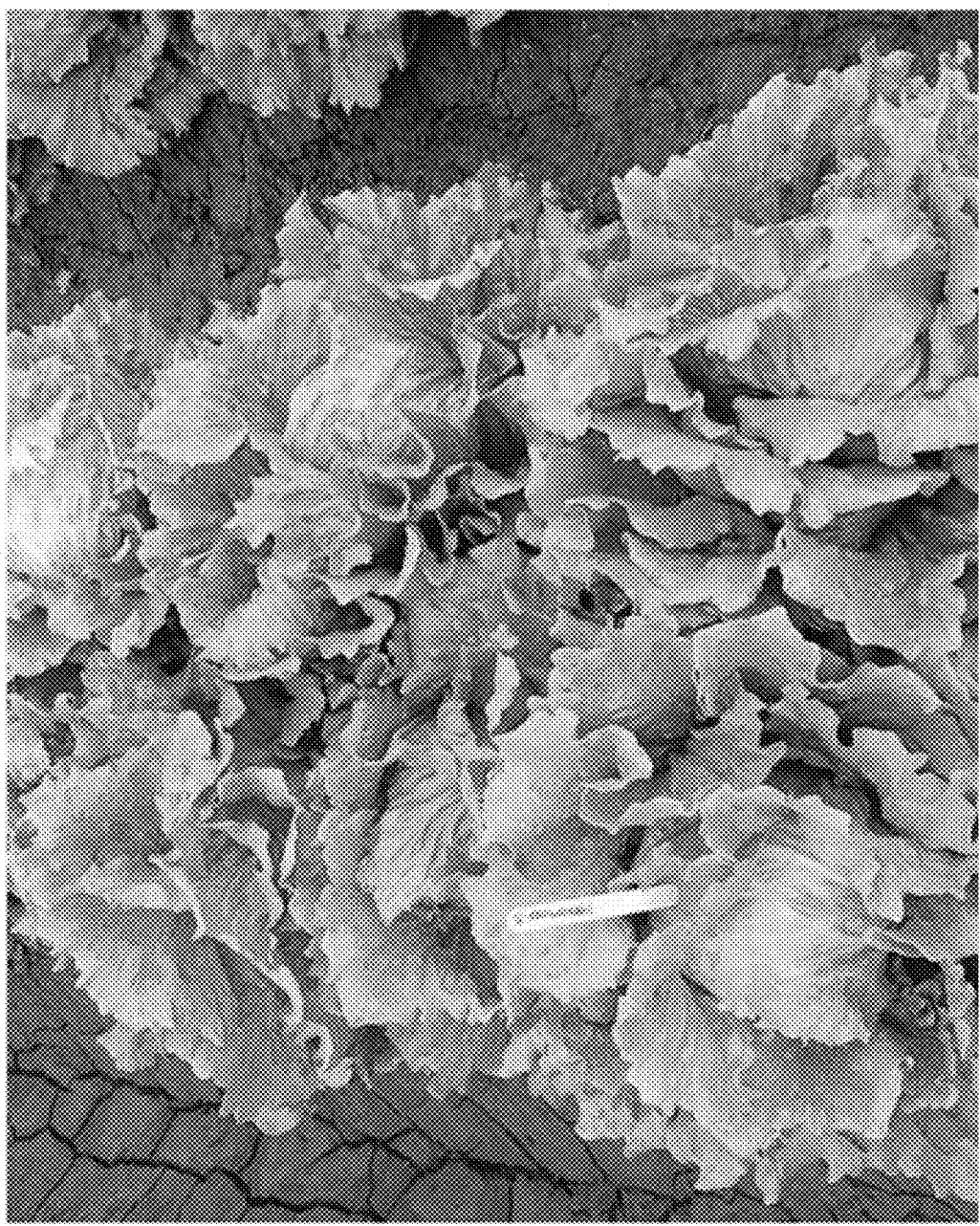
FIGS. 3A-3J show lettuce variety 'PS1519' (14RDSJV022-3).
Figure 3D:
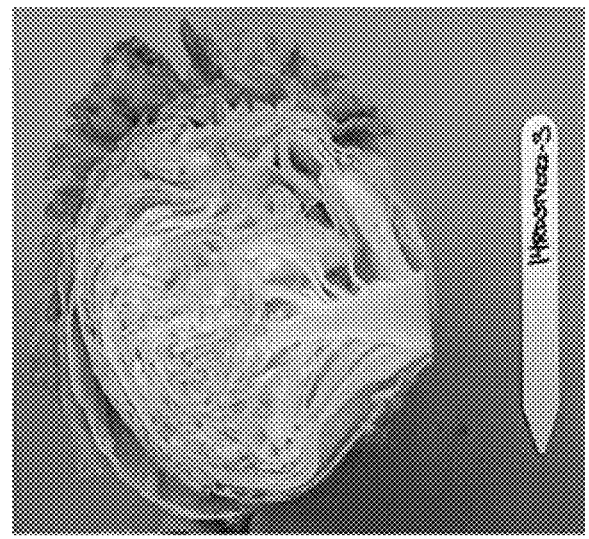
Figure 3C:
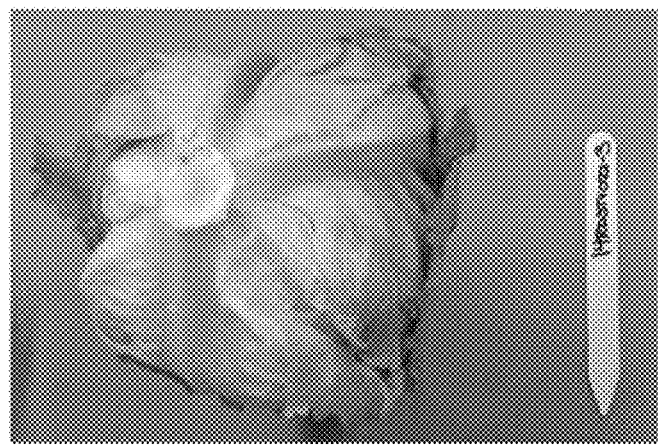
Figure 3B:
Figure 3E:
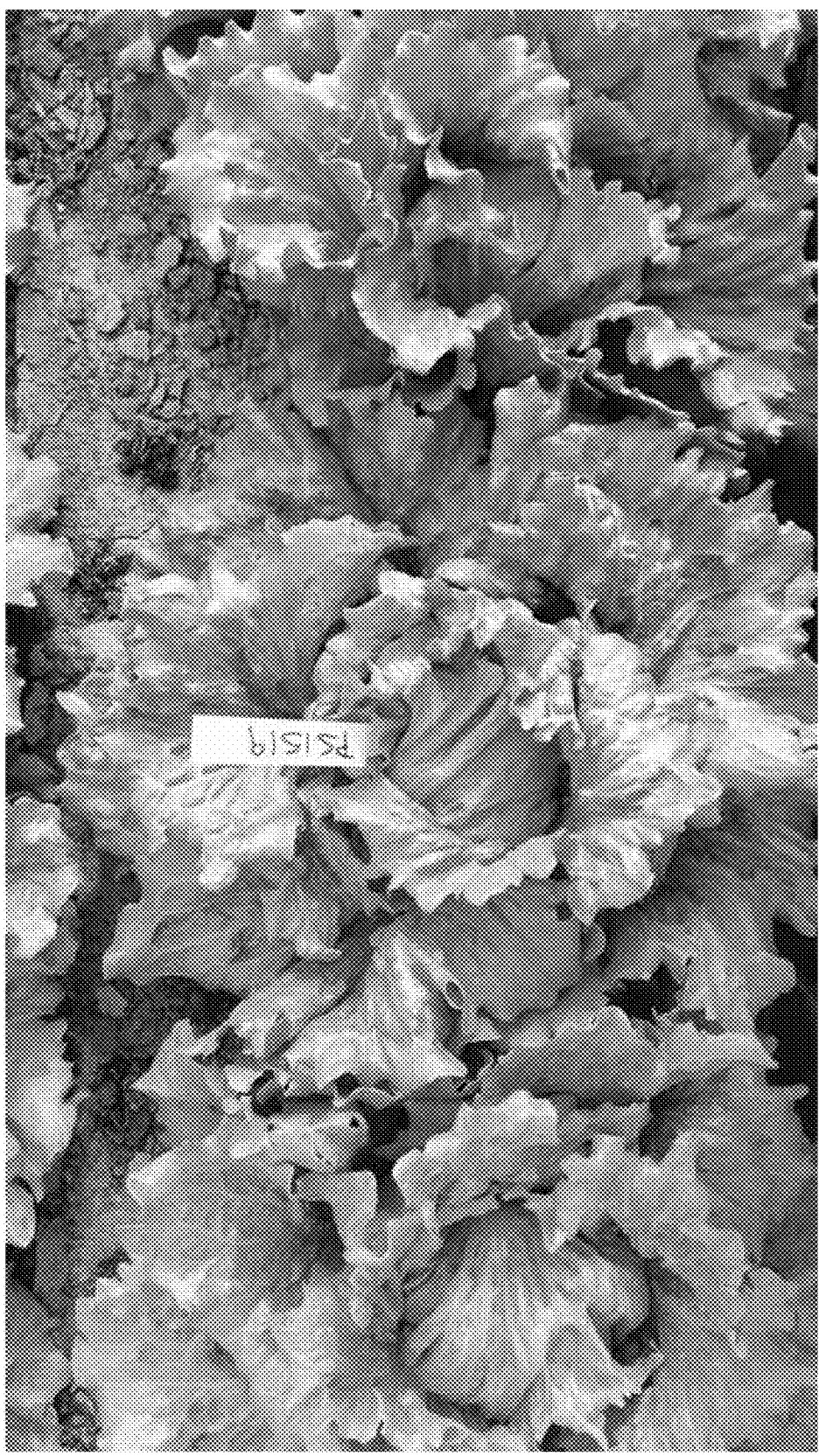
Figure 3F:
Figure 3G:
Figure 3H:
Figure 3I:
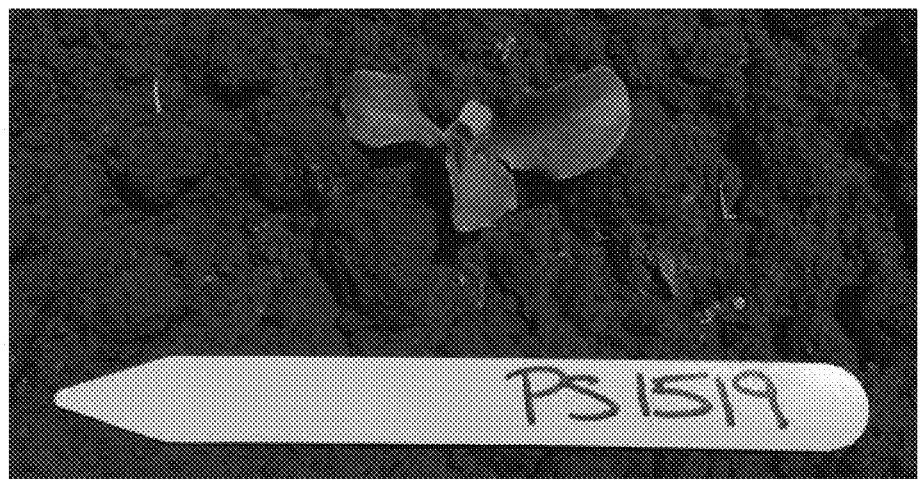
Figure 3J:

'PS1519' is an open-pollinated iceberg lettuce variety. This variety is distinct and unique to all other iceberg lettuce varieties due to its improved weight, larger frame, improved uniformity, increased head diameter, increased core diameter, and earlier bolting. Moreover, 'PS1519' has a growing season that includes autumn, and is suitable for cultivation in the open. 'PS1519' is adapted to growing in regions such as the Southwest regions of the United States, for example California and the Arizona desert. FIGS. 3A-3E and 3H depict heads of lettuce variety 'PS1519', FIG. 3I depicts a seedling of lettuce variety 'PS1519', FIGS. 3F-3G depict plants of lettuce variety 'PS1519', and FIG. 3J depicts bolting plants of lettuce variety 'PS1519'. Lettuce variety 'PS1519' is the result of numerous generations of plant selections chosen for its improved weight, larger frame, improved uniformity, and increased head diameter.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'PS1519'.

Lettuce variety 'PS1519' has the following morphologic and other characteristics:

Plant type: Crisp (i.e., iceberg); Vanguard Group
Seed:
  Color: Black
  Light dormancy: Light not required
  Heat dormancy: Susceptible
Leaves:
  Cotyledon to fourth leaf stage:
    Shape of cotyledons: Intermediate
    Shape of fourth leaf: Oval
    Apical margin: Finely dentate
    Basal margin: Coarsely dentate
    Undulation: Medium
    Green color: Dark green
    Anthocyanin:
      Distribution: Absent
      Cupping: Slight
      Reflexing: None
  Mature leaves:
    Incision depth of margin: Moderate (comparable to 'Vanguard')
    Indentation of margin: Shallowly dentate (comparable to 'Great Lakes 65')
    Undulations of the apical margin: Moderate (comparable to 'Vanguard')
    Green color of mature leaf: Munsell 5GY 6/6 (Medium green; comparable to 'Great Lakes')
    Hue of green color of mature outer leaves: Greyish
    Intensity of color of outer leaves: Light
    Anthocyanin:
      Coloration: Absent
      Distribution: Absent
      Size: Medium
      Glossiness: Moderate (comparable to 'Salinas')
      Blistering: Moderate (comparable to 'Vanguard')
      Leaf thickness: Thick
      Trichomes: Absent (smooth)
Plant:
Spread of frame leaves: 46.6 cm
Head diameter: 150.3 mm
Head shape: Spherical
Head degree of overlapping of upper part of leaves: Medium
Head size class: Medium
Head per carton: 24
Head weight: 642.4 g
Head firmness: Firm
Plant Butt:
  Shape: Flat
  Midrib: Moderately raised
Plant Core:
  Diameter at base of head: 33.5 mm
  Ratio of head diameter/core diameter: 4.5

Core height from base to head of apex: 36.5 mm
Bolting:
Class: Medium
Bolter leaves: Curved
Margin: Entire
Color: Dark green
Days from first water date to seed stalk emergence under summer conditions: 75 days
Bolter Habit
Terminal inflorescence: Present
Lateral shoots: Present
Basal side shoots: Absent
Disease/Pest Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
Pests:
*Nasonovia ribisnigri* biotype 0 (Nr:0): Susceptible
Comparisons to Other Lettuce Variety Table 6 below compares characteristics of lettuce variety 'PS1519' with the lettuce variety 'Raider'. Column 1 lists the characteristics, column 2 shows the characteristics for lettuce variety 'PS1519', and column 3 shows the characteristics for lettuce variety 'Raider'.

TABLE 6

| Characteristic | 'PS1519' | 'Raider' |
| --- | --- | --- |
| Weight | Increased weight | Lower weight |
| Frame | Larger frame | Smaller frame |
| Uniformity | Improved uniformity | Uniform |
| Bolting | Earlier | Later |
| Head diameter | Increased head diameter | Smaller head diameter |
| Core diameter | Increased core diameter | Smaller core diameter |

Table 7 below compares characteristics of lettuce variety 'PS1519' with the lettuce variety 'Raider' (PS1014). Column 1 lists the characteristics, column 2 shows the characteristics for lettuce variety 'PS1519', and column 3 shows the characteristics for lettuce variety 'Raider'.

TABLE 7

| Characteristic | 'PS1519' | 'Raider' |
| --- | --- | --- |
| Green color of mature leaves | Munsell 5GY 6/6 | Munsell 5GY 5/6 |
| Spread of frame leaves | 46.6 cm | 44.6 cm |
| Head diameter | 150.3 mm | 146 mm |
| Head weight | 642.4 g | 589.1 g |
| Diameter at base of head | 33.5 mm | 31.8 mm |
| Core height from base to apex | 36.5 mm | 33.7 mm |

Tables 8A and 8B below show results of a first trial that compares the head weight, head diameter, core length, core diameter, and frame diameter of 20 plants of the lettuce variety 'PS1519' (Table 8A) with those of 20 plants of lettuce variety 'Raider' (Table 8B).

TABLE 8A

| 'PS1519' | Head Wt. | Head Diameter | Core Length | Core Diameter | Frame Diameter |
| --- | --- | --- | --- | --- | --- |
| Max | 1050 g | 162 mm | 47 mm | 39 mm | 54 cm |
| Min | 480 g | 131 mm | 27 mm | 27 mm | 47 cm |
| Average | 708.75 g | 148.9 mm | 36.5 mm | 32.5 mm | 50.7 cm |
| Std. Dev | 181.25 | 9.63 | 7.02 | 3.63 | 1.98 |

TABLE 8B

| 'Raider' | Head Wt. | Head Diameter | Core Length | Core Diameter | Frame Diameter |
| --- | --- | --- | --- | --- | --- |
| Max | 855 g | 164 mm | 49 mm | 34 mm | 52 cm |
| Min | 430 g | 124 mm | 27 mm | 28 mm | 45 cm |
| Average | 663.25 g | 147.25 mm | 37.35 mm | 31.4 mm | 48.8 cm |
| Std. Dev | 116.27 | 9.33 | 5.35 | 1.85 | 2.24 |

Tables 9A and 9B below show results of a second trial that compares the head weight, head diameter, core length, core diameter, frame diameter, and head length of 20 plants of the lettuce variety 'PS1519' (Table 9A) with those of 20 plants of lettuce variety 'Raider' (Table 9B).

TABLE 9A

| 'PS1519' | Head Wt. | Head Diameter | Core Length | Core Diameter | Frame Diameter | Head Length |
| --- | --- | --- | --- | --- | --- | --- |
| Max | 735 g | 175 mm | 56 mm | 37 mm | 48 cm | 159 mm |
| Min | 405 g | 130 mm | 18 mm | 30 mm | 38 cm | 125 mm |
| Average | 576 g | 151.6 mm | 36.5 mm | 34.55 mm | 42.5 cm | 144.65 mm |
| Std. Dev | 90.74 | 10.63 | 8.87 | 2.01 | 2.65 | 9.19 |

TABLE 9B

| 'Raider' | Head Wt. | Head Diameter | Core Length | Core Diameter | Frame Diameter | Head Length |
|---|---|---|---|---|---|---|
| Max | 665 g | 162 mm | 43 mm | 36 mm | 46 cm | 151 mm |
| Min | 355 g | 125 mm | 22 mm | 28 mm | 36 cm | 130 mm |
| Average | 515 g | 144.75 mm | 29.95 mm | 32.15 mm | 40.3 cm | 139.6 mm |
| Std. Dev | 82.30 | 10.95 | 5.73 | 2.37 | 2.56 | 7.04 |

Figure 4A:
FIGS. 4A-4P show a comparison between lettuce varieties 'Raider' (PS1014) and 'PS1519' (14RDSJV022-3).
Figure 4B:
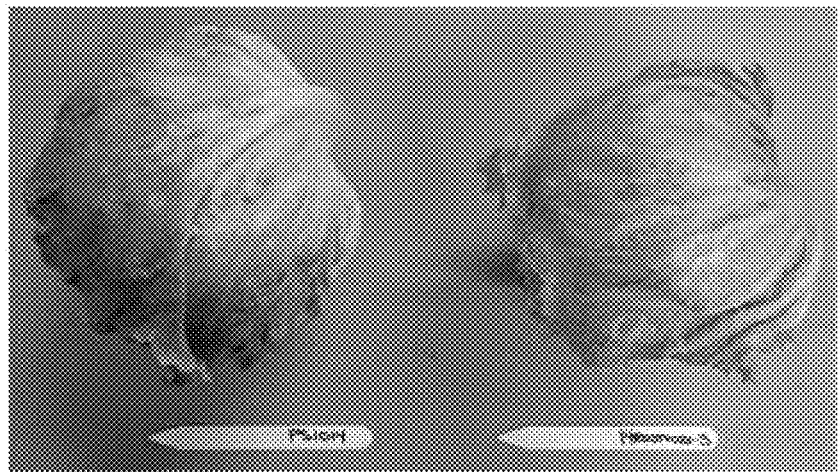
FIG. 4B shows a side view of heads of lettuce varieties 'Raider' (PS1014; on left) and 'PS1519' (14RDSJV022-3; on right).
Figure 4C:
FIG. 4C shows a bottom view of heads of lettuce varieties 'Raider' (PS1014; on left) and 'PS1519' (14RDSJV022-3; on right).
Figure 4D:
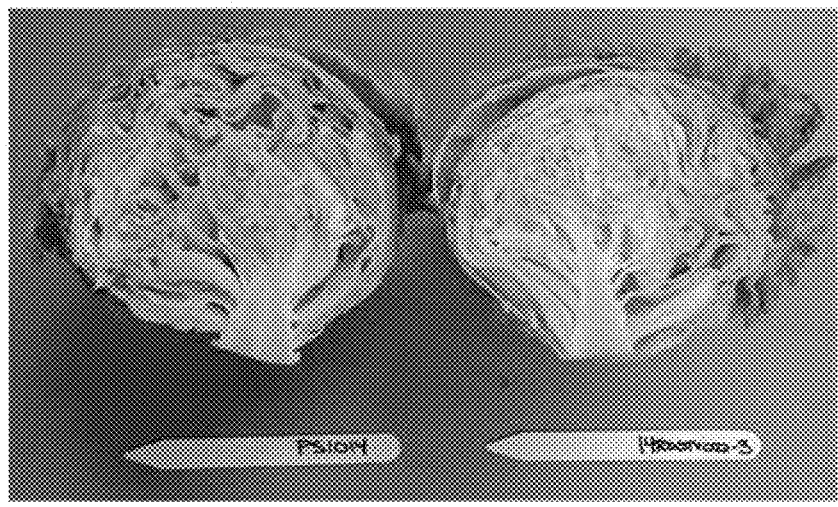
FIG. 4D shows a cross-sectional view of heads of lettuce varieties 'Raider' (PS1014; on left) and 'PS1519' (14RDSJV022-3; on right).
Figure 4E:
FIG. 4E shows a bottom view of heads of lettuce varieties 'Raider' (PS1014; on left) and 'PS1519' (on right).
Figure 4F:
FIG. 4F shows a side view of heads of lettuce varieties 'Raider' (PS1014; on left) and 'PS1519' (on right).
Figure 4G:
FIG. 4G shows a bottom view of heads of lettuce varieties 'Raider' (PS1014; on left) and 'PS1519' (14RDSJV022-3; on right).
Figure 4H:
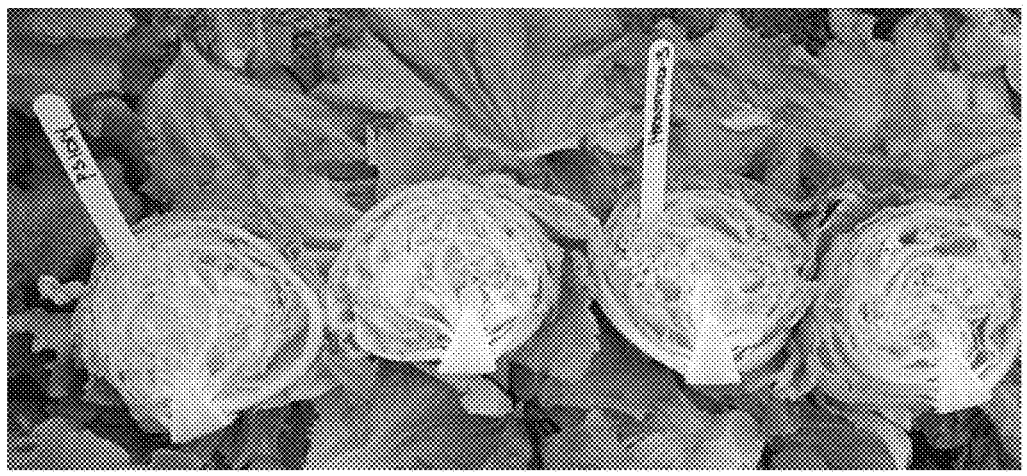
FIG. 4H shows cross-sectional views of heads of lettuce varieties 'Raider' (PS1014; two on left) and 'PS1519' (14RDSJV022-3; two on right).
Figure 4I:
FIG. 4I shows bottom and cross-sectional views of heads of lettuce variety 'Raider' (PS1014).
Figure 4J:
FIG. 4J shows a seedling of lettuce variety 'Raider' (PS1014).
Figure 4K:
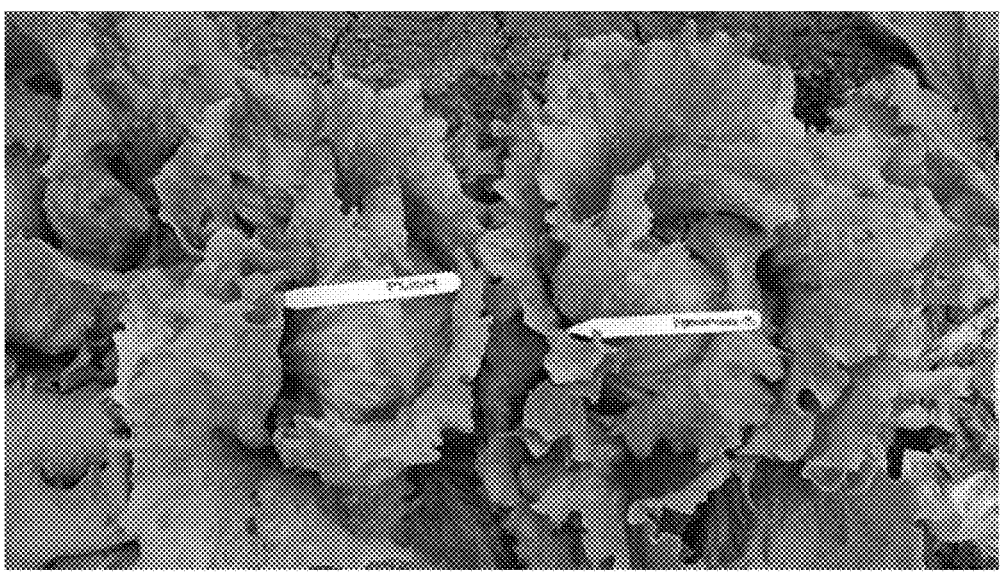
FIG. 4K shows heads of lettuce varieties 'Raider' (PS1014; on left) and 'PS1519' (14RDSJV022-3; on right).
Figure 4L:
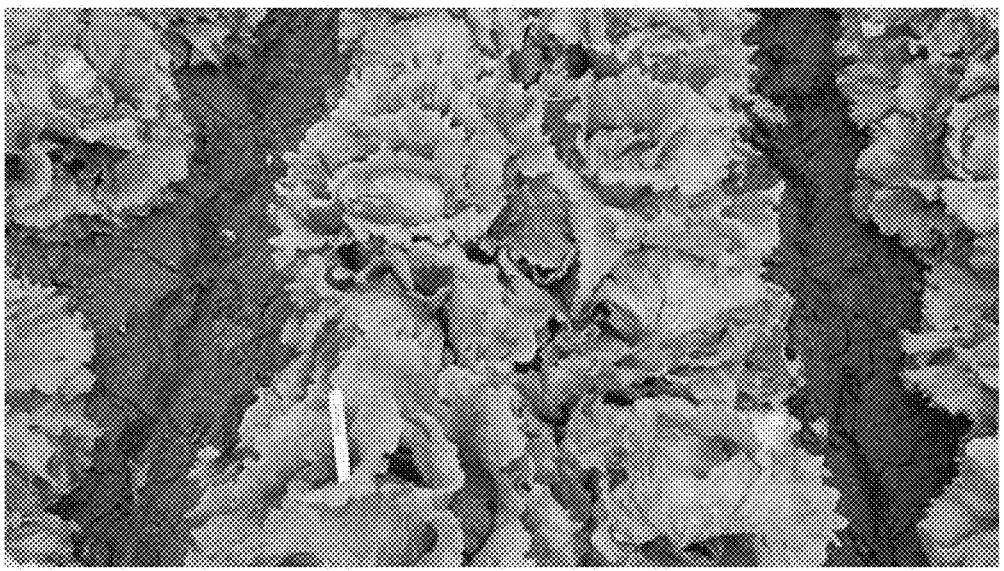
FIG. 4L shows heads of lettuce variety 'Raider' (PS1014).
Figure 4M:
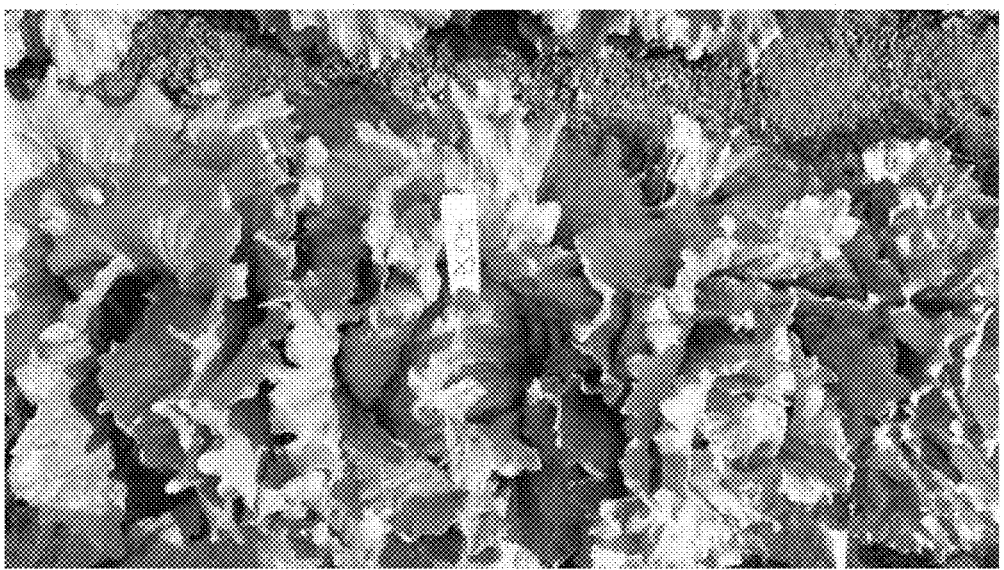
FIG. 4M shows heads of lettuce variety 'Raider' (PS1014).
Figure 4N:
FIG. 4N shows plants of lettuce variety 'Raider' (PS1014).
Figure 4O:
FIG. 4O shows plants of lettuce variety 'Raider'.
Figure 4P:

Further distinguishing features are apparent from the comparison of the two varieties depicted in FIGS. 4A-4P.

Objective Description of the Variety 'Elevate'

Figure 5A:
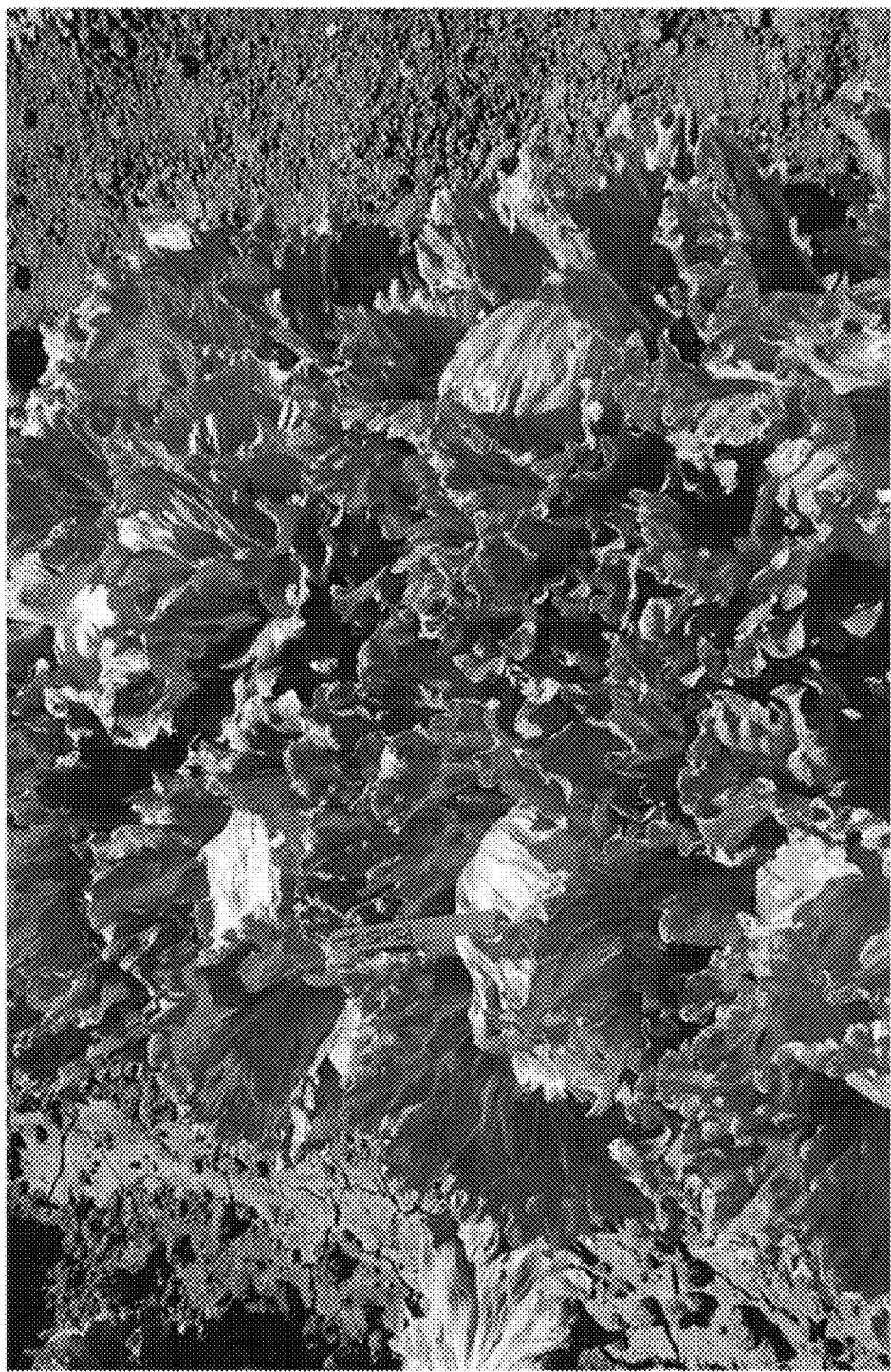
FIGS. 5A-5M show lettuce variety 'Elevate' (PS1512).
Figure 5C:
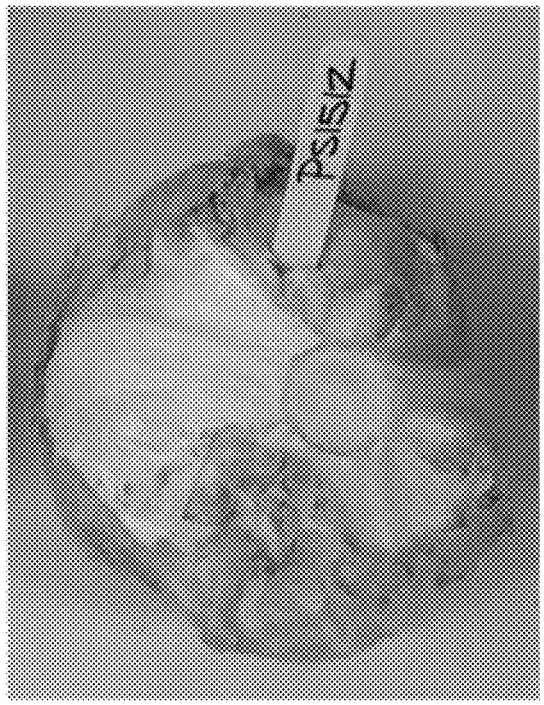
Figure 5B:
Figure 5D:
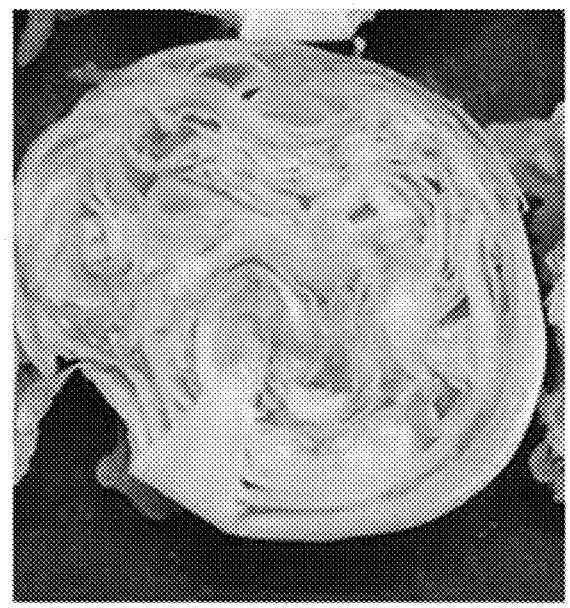
Figure 5E:
Figure 5F:
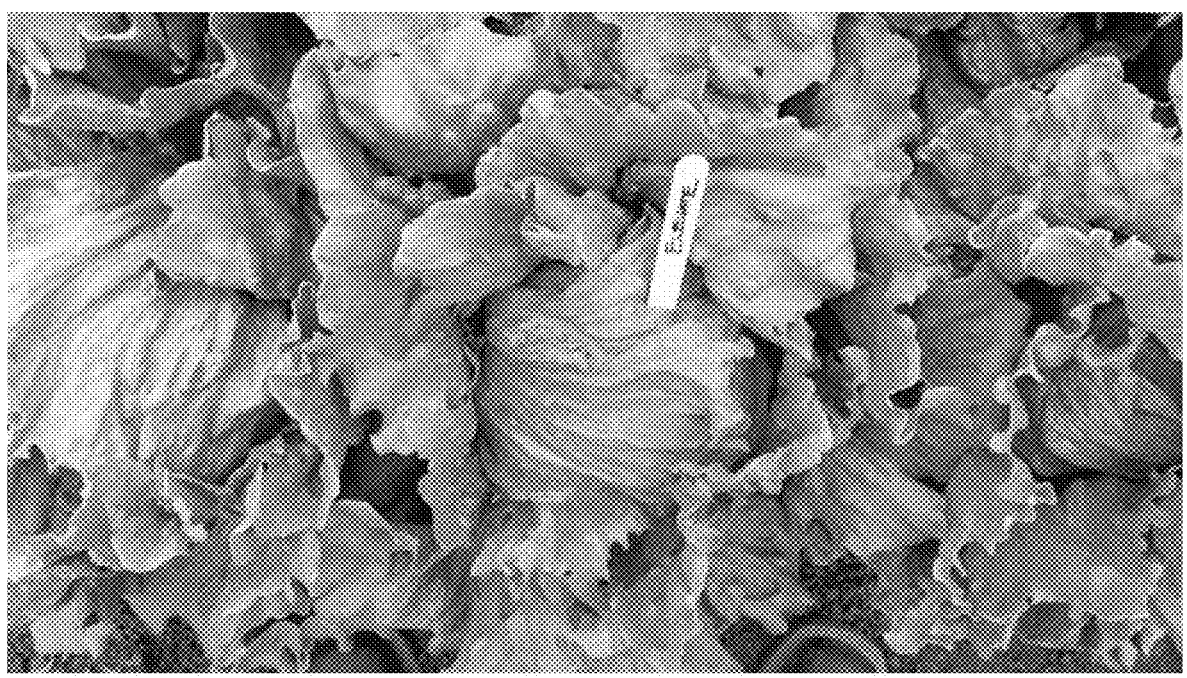
Figure 5G:
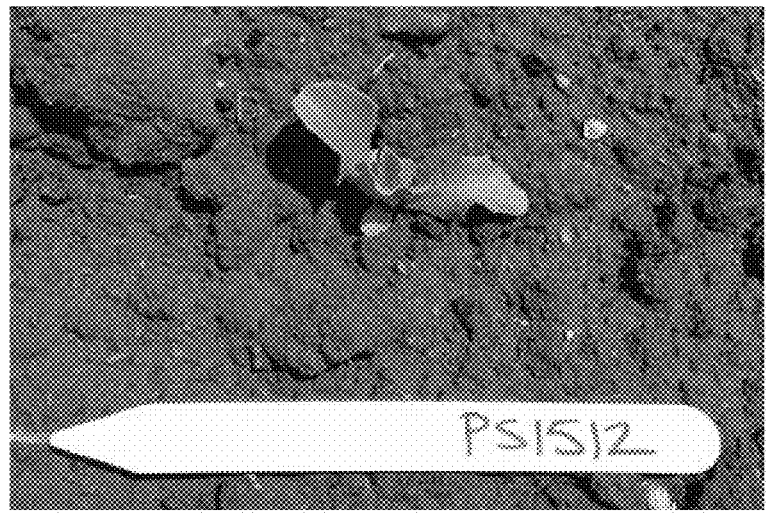
Figure 5H:
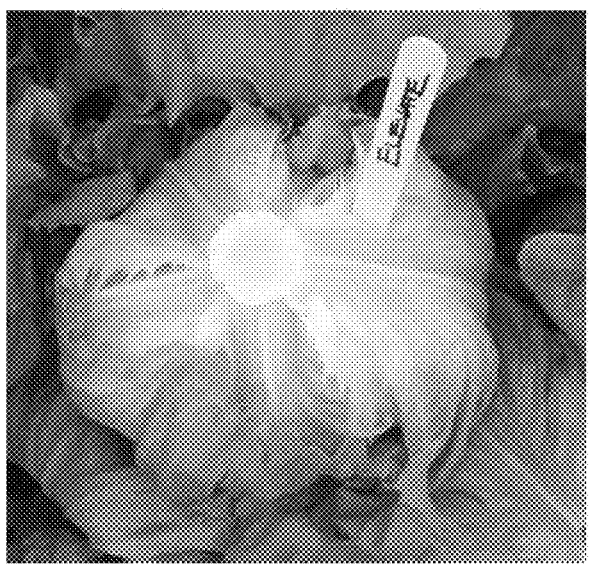
Figure 5I:
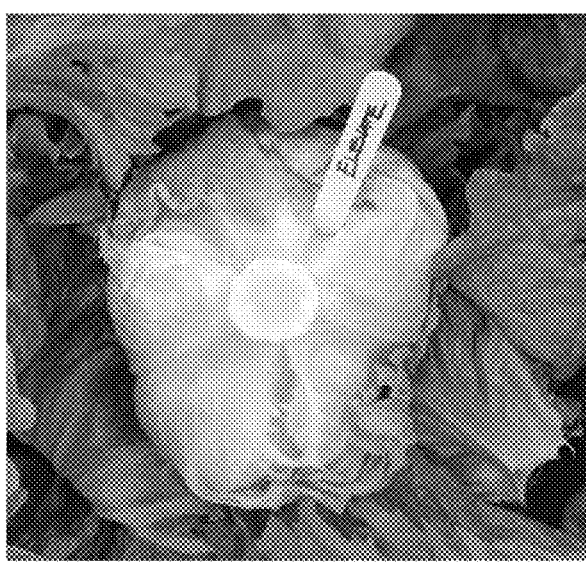
Figure 5J:
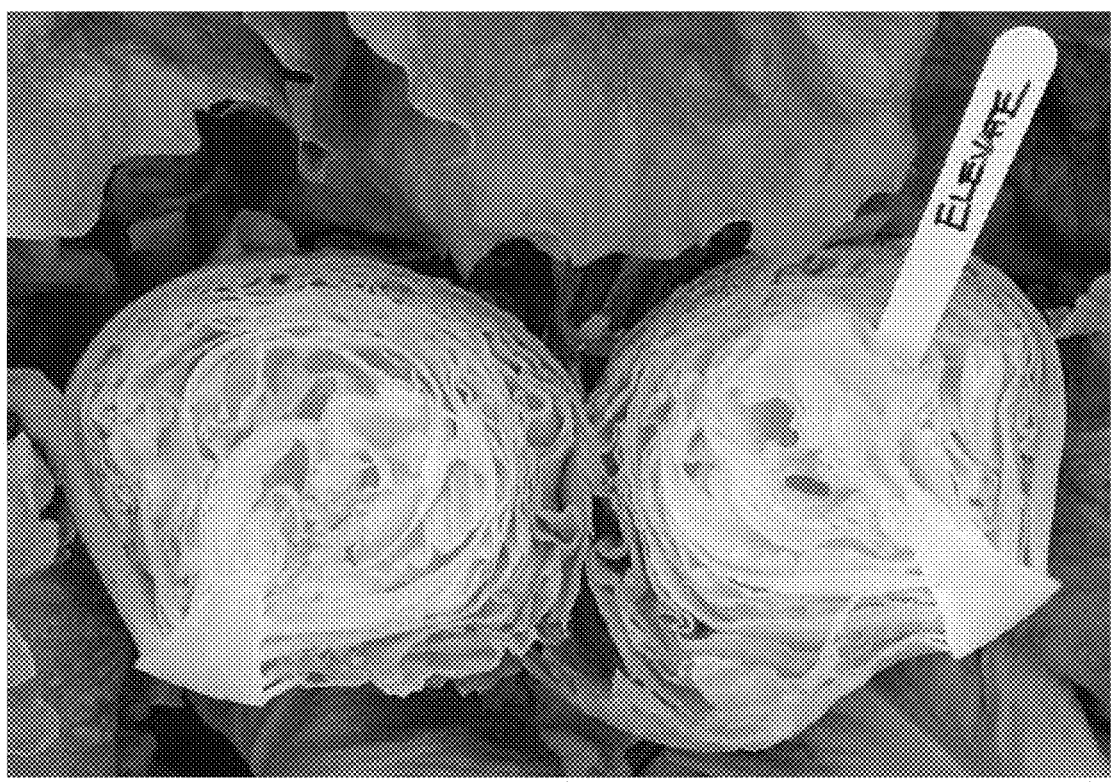
Figure 5K:
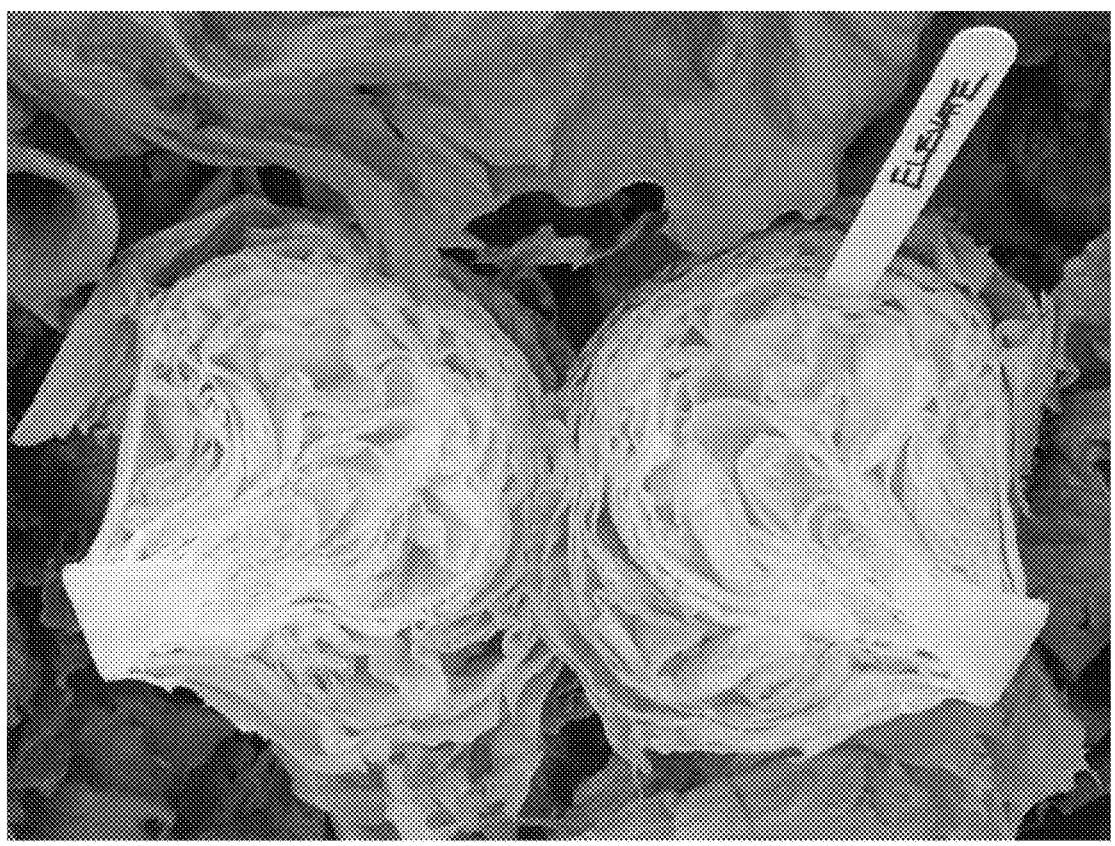
Figure 5L:
Figure 5M:

'Elevate' is an open-pollinated iceberg lettuce variety. This variety is distinct and unique to all other iceberg lettuce varieties due to its lighter green color, improved uniformity, larger head diameter, larger stem length, increased head weight, increased core diameter, and smaller frame size. Moreover, 'Elevate' has a growing season that includes winter, and is suitable for cultivation in the open. 'Elevate' is adapted to growing in regions such as the Southwest regions of the United States, for example California and the Arizona desert. FIGS. 5A-5D, 5F, and 5H-5L depict heads of lettuce variety 'Elevate', FIG. 5G depicts a seedling of lettuce variety 'Elevate', FIG. 5E depicts plants of lettuce variety 'Elevate', and FIG. 5M depicts bolting plants of lettuce variety 'Elevate'. Lettuce variety 'Elevate' is the result of numerous generations of plant selections chosen for its lighter green color, improved uniformity, larger head diameter, and increased head weight.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Elevate'.

Lettuce variety 'Elevate' has the following morphologic and other characteristics:

Plant type: Crisp (i.e., iceberg); Salinas Group
Seed:
Color: Black
Leaves:
Cotyledon to fourth leaf stage:
    Shape of cotyledons: Intermediate
    Shape of fourth leaf: Oval
    Apical margin: Finely dentate
    Basal margin: Moderately dentate
    Undulation: Slight
    Green color: Dark green
    Anthocyanin:
        Distribution: Absent
        Cupping: Slight
        Reflexing: None
Mature leaves:
    Incision depth of margin: Moderate (comparable to 'Vanguard')
    Indentation of margin: Shallowly dentate (comparable to 'Great Lakes 65')
    Undulations of the apical margin: Moderate (comparable to 'Vanguard')
    Green color: Munsell 5GY 6/6 (Medium green; comparable to 'Great Lakes')
    Hue of green color of mature outer leaves: Greyish
    Intensity of color of outer leaves: Medium
    Anthocyanin:
        Coloration: Absent
        Distribution: Absent
        Size: Medium
        Glossiness: Moderate (comparable to 'Salinas')
        Blistering: Absent/slight (comparable to 'Salinas')
        Leaf thickness: Thick
        Trichomes of mature leaf: Absent (smooth)
Plant:
Spread of frame leaves: 47.9 cm
Head diameter: 168.2 mm
Head shape: Spherical
Head degree of overlapping of upper part of leaves: Strong
Head size class: Medium
Head per carton: 24
Head weight: 722.5 g
Head firmness: Moderate
Plant Butt:
Shape: Flat
Midrib: Flattened (comparable to 'Salinas')
Plant Core:
Diameter at base of head: 34.6 mm
Ratio of head diameter/core diameter: 4.8
Core height from base of head to apex: 41.9 mm
Bolting:
Class: Medium
Bolter leaves: Curved
Margin: Entire
Color: Medium green
Days from first water date to seed stalk emergence under summer conditions: 69 days
Bolter Habit:
Lateral shoots: Present
Basal side shoots: Absent
Disease/Pest Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
Pests:
    *Nasonovia ribisnigri* biotype 0 (Nr:0): Susceptible
Comparisons to Other Lettuce Variety Table 10 below compares characteristics of lettuce variety 'Elevate' with the lettuce variety 'Gun Slinger' (U.S. Pat. No. 8,362,326). Column 1 lists the characteristics, column 2 shows the characteristics for lettuce variety 'Elevate', and column 3 shows the characteristics for lettuce variety 'Gun Slinger'.

TABLE 10

| Characteristic | 'Elevate' | 'Gun Slinger' |
|---|---|---|
| Leaf color | Lighter green color | Darker green color |
| Uniformity | Improved uniformity | Uniform |
| Head diameter | Larger head diameter | Smaller head diameter |
| Stem length | Larger stem length | Smaller stem length |
| Frame size | Smaller frame size | Larger frame size |
| Head weight | Increased head weight | Lower head weight |
| Core diameter | Larger core diameter | Smaller core diameter |

Table 11 below compares characteristics of lettuce variety 'Elevate' with the lettuce variety 'Gun Slinger' (PS1013). Column 1 lists the characteristics, column 2 shows the characteristics for lettuce variety 'Elevate', and column 3 shows the characteristics for lettuce variety 'Gun Slinger'.

TABLE 11

| Characteristic | 'Elevate' | 'Gun Slinger' |
|---|---|---|
| Green color of mature leaves | Munsell 5GY 6/6 | Munsell 5GY 5/6 |
| Spread of frame leaves | 47.9 cm | 49.0 cm |
| Head diameter | 168.2 mm | 161.7 mm |
| Head weight | 722.5 g | 632.4 g |
| Diameter at base of head | 34.6 mm | 32.9 mm |
| Core height from base to apex | 41.9 mm | 37.2 mm |

Tables 12A and 12B below show results of a first trial that compares the head weight, head diameter, core length, core diameter, frame diameter, and head length of 20 plants of the lettuce variety 'Elevate' (Table 12A) with those of 20 plants of lettuce variety 'Gun Slinger' (Table 12B).

TABLE 12A

| 'Elevate' | Head Wt. | Head Diameter | Core Length | Core Diameter | Frame Diameter | Head Length |
|---|---|---|---|---|---|---|
| Max | 1020 g | 193 mm | 47 mm | 38 mm | 52 cm | 168 mm |
| Min | 610 g | 158 mm | 31 mm | 34 mm | 42 cm | 138 mm |
| Average | 825.75 g | 174.15 mm | 39.35 mm | 36.5 mm | 47.8 cm | 155.15 mm |
| Std. Dev | 105.41 | 9.08 | 3.69 | 1.28 | 2.82 | 7.64 |

TABLE 12B

| 'Gun Slinger' | Head Wt. | Head Diameter | Core Length | Core Diameter | Frame Diameter | Head Length |
|---|---|---|---|---|---|---|
| Max | 790 g | 197 mm | 41 mm | 37 mm | 52 cm | 158 mm |
| Min | 435 g | 140 mm | 28 mm | 32 mm | 45 cm | 130 mm |
| Average | 631.5 g | 163.25 mm | 33.95 mm | 34.5 mm | 48.65 cm | 143 mm |
| Std. Dev | 102.68 | 14.95 | 3.43 | 1.47 | 1.95 | 7.18 |

Tables 13A and 13B below show results of a second trial that compares the head weight, head diameter, core length, core diameter, frame diameter, and head length of 20 plants of the lettuce variety 'Elevate' (Table 13A) with those of 20 plants of lettuce variety 'Gun Slinger' (Table 13B).

TABLE 13A

| 'Elevate' | Head Wt. | Head Diameter | Core Length | Core Diameter | Frame Diameter | Head Length |
|---|---|---|---|---|---|---|
| Max | 870 g | 173 mm | 60 mm | 38 mm | 50.5 cm | 157 mm |
| Min | 515 g | 144 mm | 38 mm | 32 mm | 43.5 cm | 123 mm |
| Average | 697.75 g | 157.75 mm | 48.3 mm | 35.2 mm | 46.05 cm | 144.7 mm |
| Std. Dev | 92.87 | 6.10 | 5.94 | 1.58 | 2.12 | 9.29 |

TABLE 13B

| 'Gun Slinger' | Head Wt. | Head Diameter | Core Length | Core Diameter | Frame Diameter | Head Length |
|---|---|---|---|---|---|---|
| Max | 720 g | 173 mm | 50 mm | 36 mm | 51 cm | 153 mm |
| Min | 465 g | 135 mm | 34 mm | 29 mm | 43.5 cm | 128 mm |
| Average | 619 g | 157.2 mm | 40.7 mm | 33.3 mm | 46.65 cm | 142.4 mm |
| Std. Dev | 66.90 | 9.70 | 4.57 | 1.42 | 2.41 | 7.42 |

Tables 14A and 14B below show results of a third trial that compares the head weight, head diameter, core length, core diameter, and frame diameter of 20 plants of the lettuce variety 'Elevate' (Table 14A) with those of 20 plants of lettuce variety 'Gun Slinger' (Table 14B).

TABLE 14A

| 'Elevate' | Head Wt. | Head Diameter | Core Length | Core Diameter | Frame Diameter |
|---|---|---|---|---|---|
| Max | 793 g | 205 mm | 45 mm | 37 mm | 54 cm |
| Min | 501 g | 148 mm | 32 mm | 28 mm | 43.5 cm |
| Average | 644.1 g | 172.6 mm | 38.2 mm | 31.95 mm | 50.13 cm |
| Std. Dev | 77.76 | 15.30 | 3.94 | 2.01 | 2.44 |

TABLE 14B

| 'Gun Slinger' | Head Wt. | Head Diameter | Core Length | Core Diameter | Frame Diameter |
|---|---|---|---|---|---|
| Max | 830 g | 185 mm | 45 mm | 37 mm | 54.5 cm |
| Min | 510 g | 143 mm | 29 mm | 28 mm | 46 cm |
| Average | 646.75 g | 164.6 mm | 36.85 mm | 31.15 mm | 51.8 cm |
| Std. Dev | 94.07 | 15.08 | 3.92 | 2.74 | 2.23 |

Figure 6A:
FIGS. 6A-6P show a comparison between lettuce varieties 'Gun Slinger' (PS1013; U.S. Pat. No. 8,362,326) and 'Elevate' (PS1512).
Figure 6B:
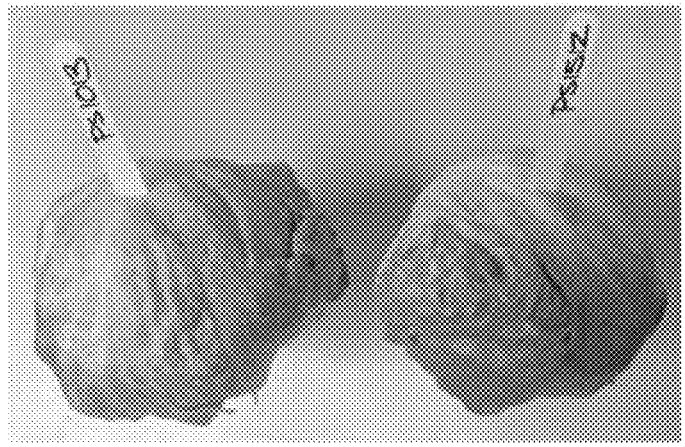
FIG. 6B shows a top view of heads of lettuce varieties 'Gun Slinger' (PS1013; on left) and 'Elevate' (PS1512; on right).
Figure 6C:
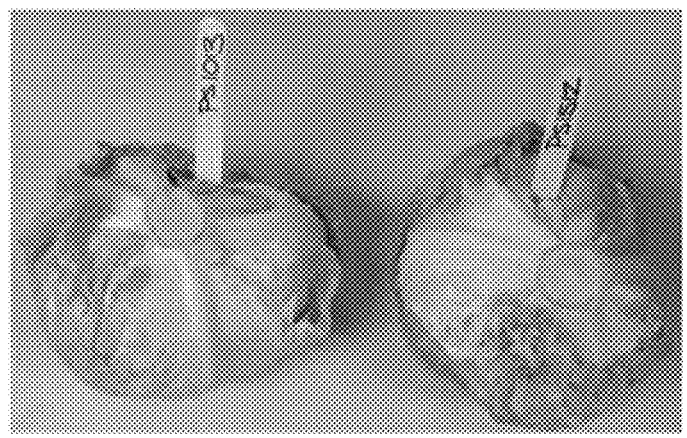
FIG. 6C shows a bottom view of heads of lettuce varieties 'Gun Slinger' (PS1013; on left) and 'Elevate' (PS1512; on right).
Figure 6D:
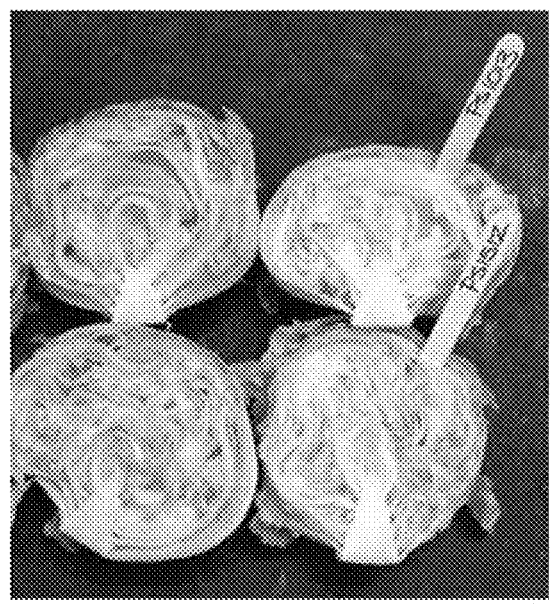
FIG. 6D shows cross-sectional views of heads of lettuce varieties 'Gun Slinger' (PS1013; top row) and 'Elevate' (PS1512; bottom row).
Figure 6E:
FIG. 6E shows side views of heads of lettuce varieties 'Elevate' (top row) and 'Gun Slinger' (bottom row).
Figure 6F:
FIG. 6F shows top views of heads of lettuce varieties 'Elevate' (top row) and 'Gun Slinger' (bottom row).
Figure 6G:
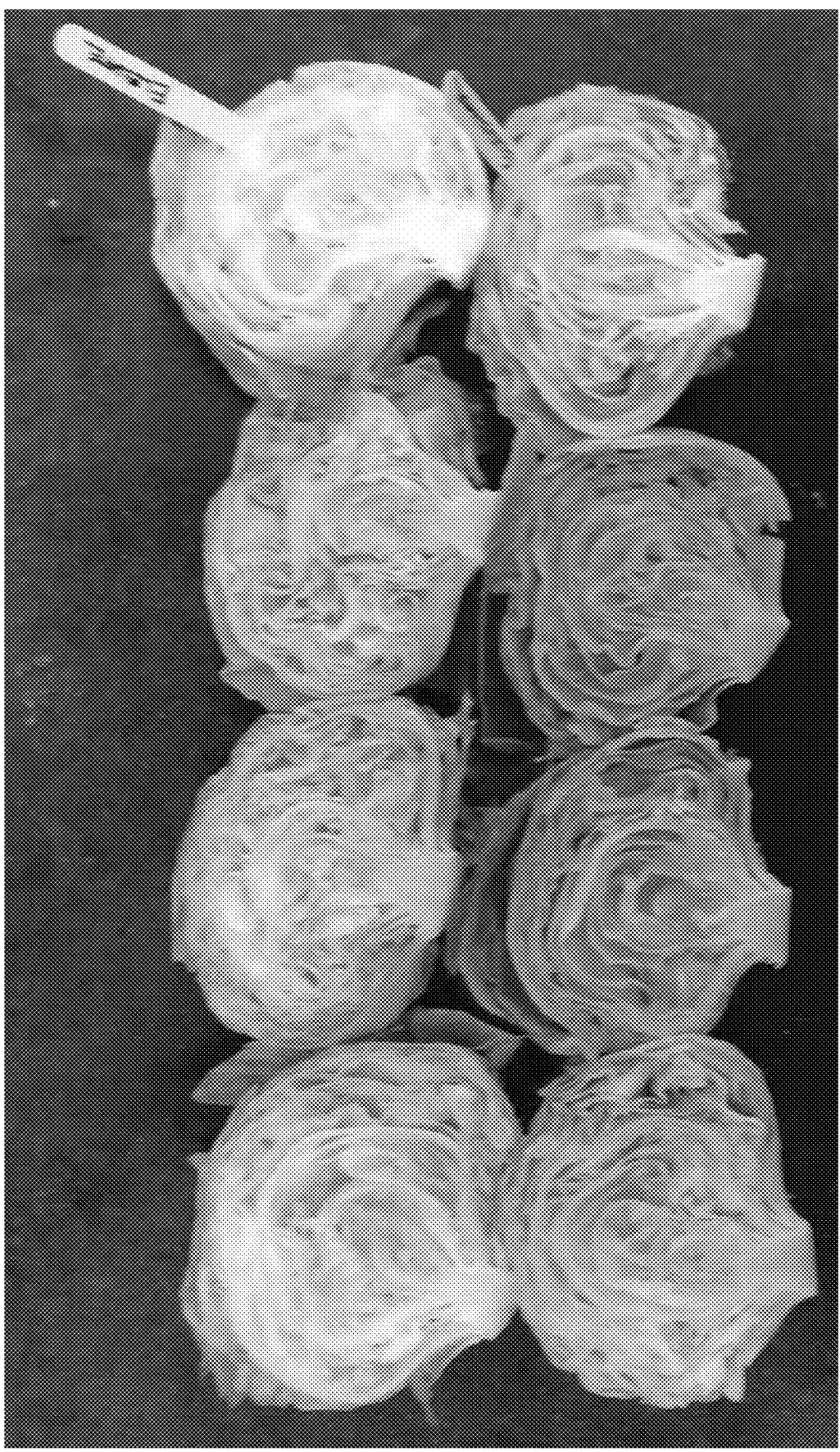
FIG. 6G shows cross-sectional views of heads of lettuce varieties 'Elevate' (top row) and 'Gun Slinger' (bottom row).
Figure 6H:
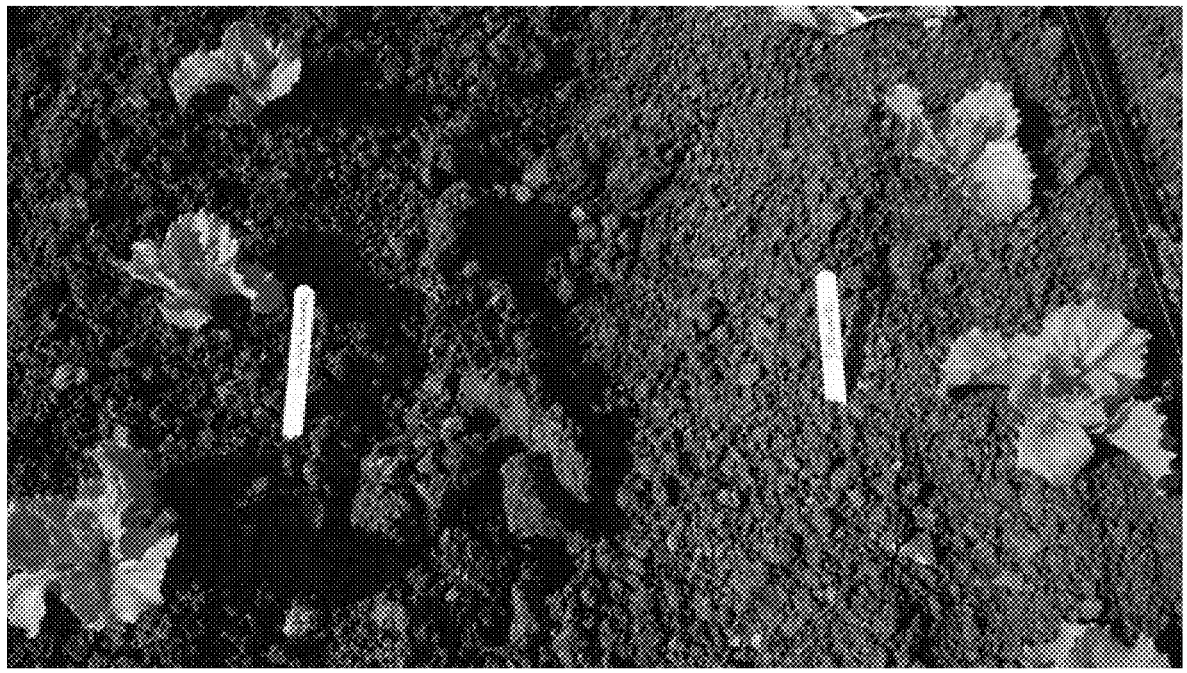
FIG. 6H shows seedlings of lettuce varieties 'Elevate' (right column) and 'Gun Slinger' (left column).
Figure 6I:
FIG. 6I shows a seedling of lettuce variety 'Gun Slinger' (PS1013).
Figure 6J:
FIG. 6J shows plants of lettuce variety 'Gun Slinger' (PS1013).
Figure 6K:
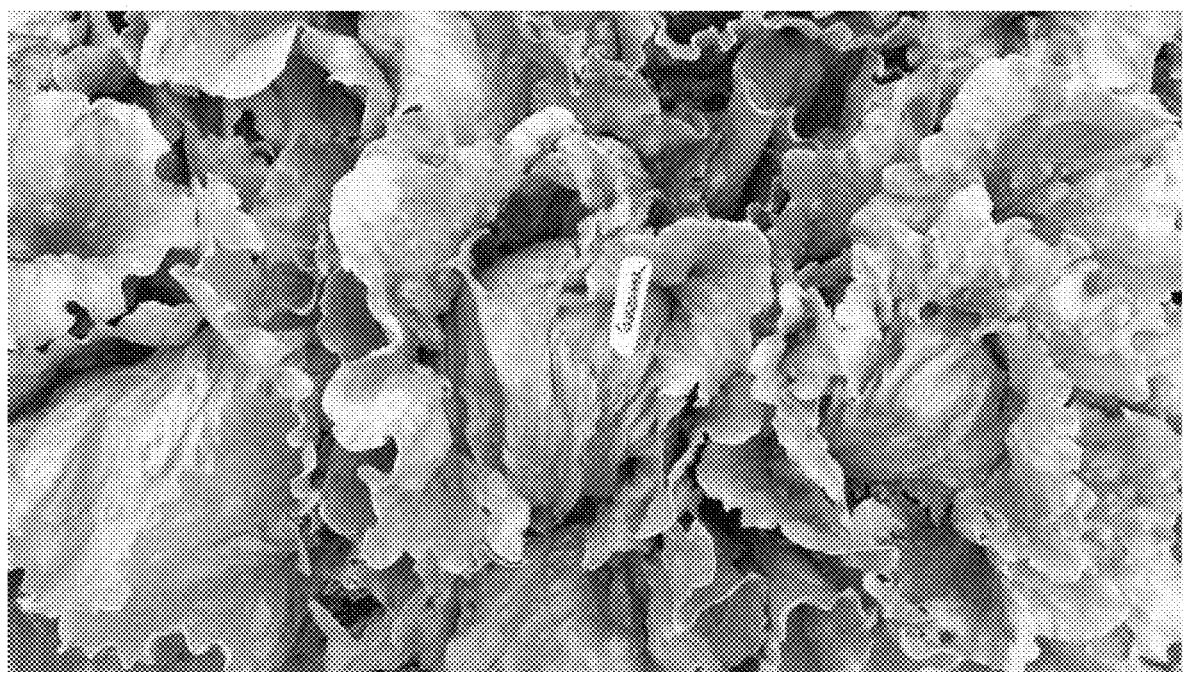
FIG. 6K shows heads of lettuce variety 'Gun Slinger'.
Figure 6L:
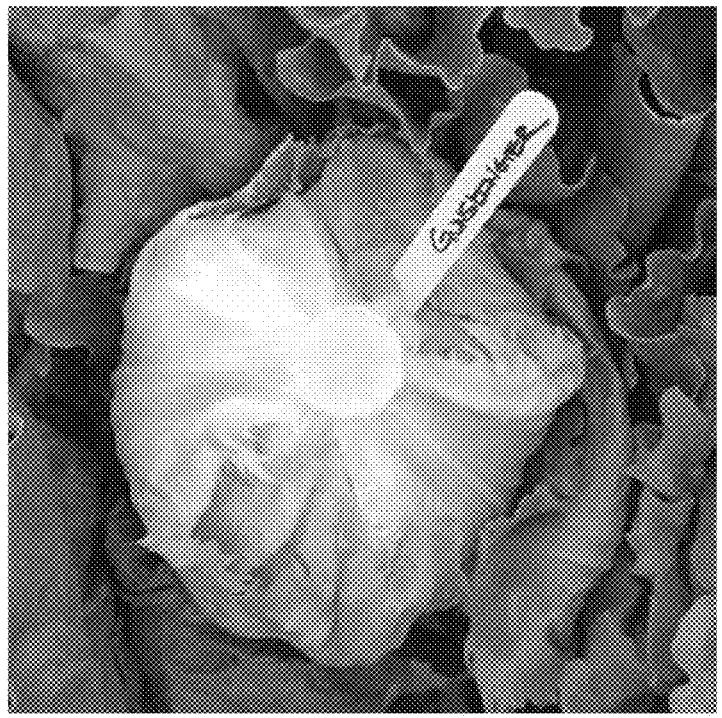
FIG. 6L shows a bottom view of a head of lettuce variety 'Gun Slinger'.
Figure 6M:
FIG. 6M shows a cross-sectional view of a head of lettuce variety 'Gun Slinger'.
Figure 6N:
FIG. 6N shows heads of lettuce varieties 'Elevate' (right carton) and 'Gun Slinger' (left carton) in cartons.
Figure 6O:
FIG. 6O shows heads of lettuce variety 'Gun Slinger' in a carton.
Figure 6P:

Further distinguishing features are apparent from the comparison of the two varieties depicted in FIGS. 6A-6P.

Objective Description of the Variety 'Payday'

Figure 7A:
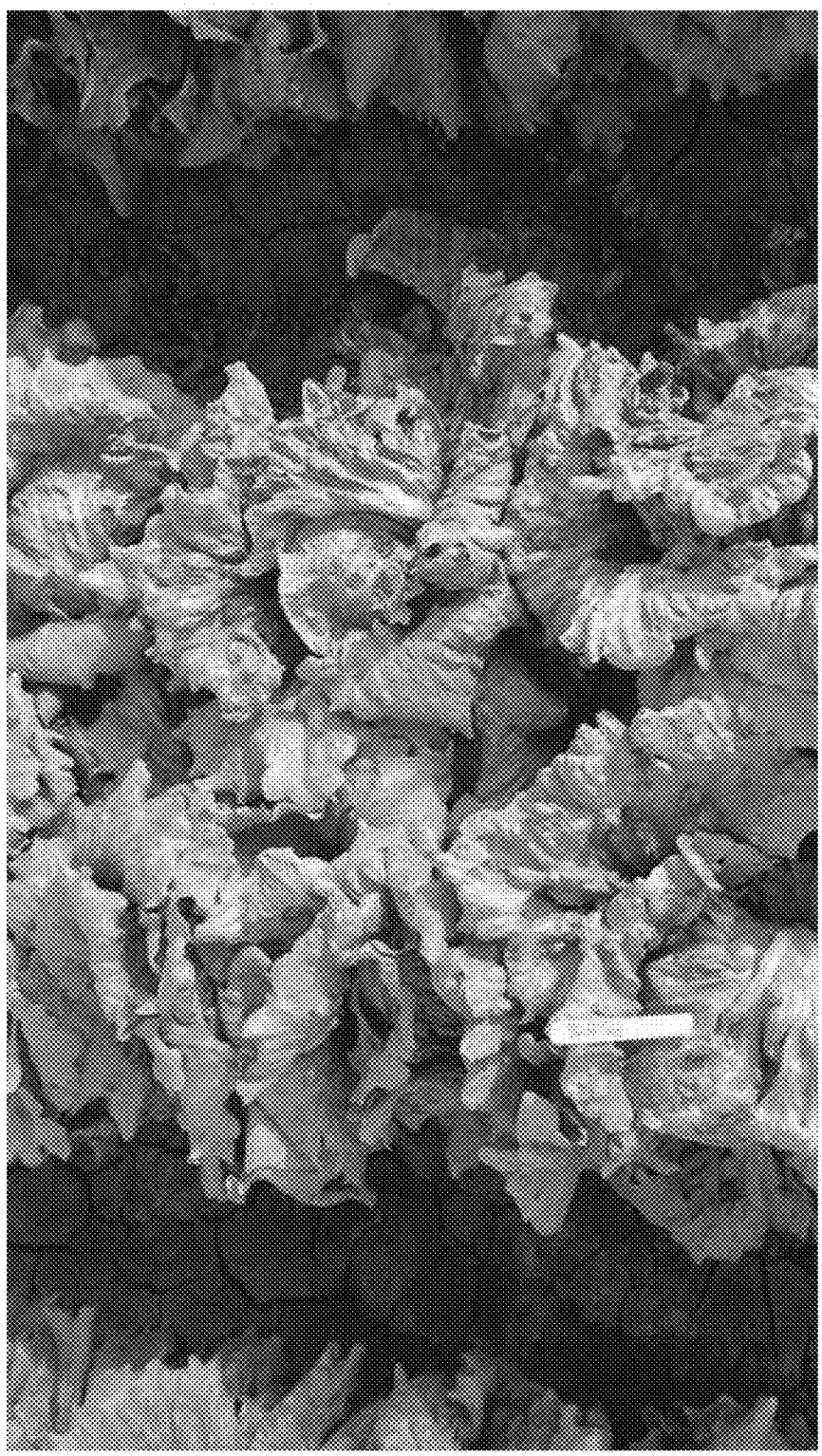
Figure 7B:
Figure 7C:
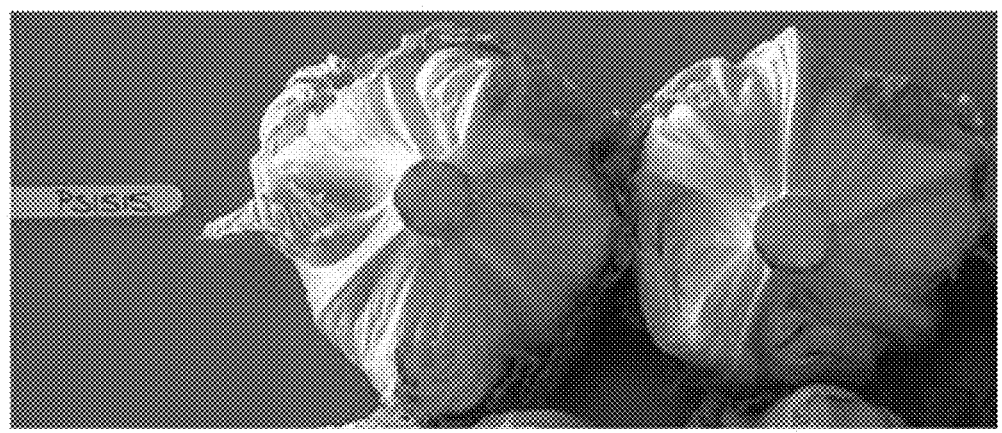
Figure 7D:
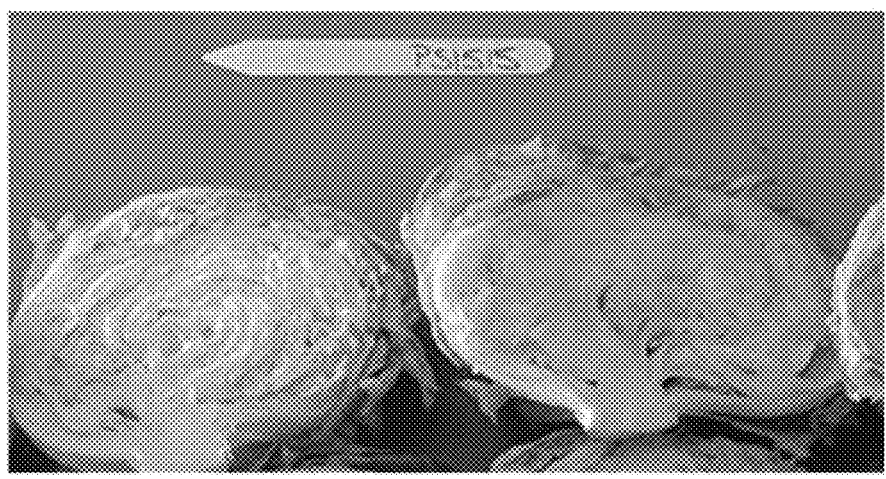
Figure 7E:
Figure 7F:
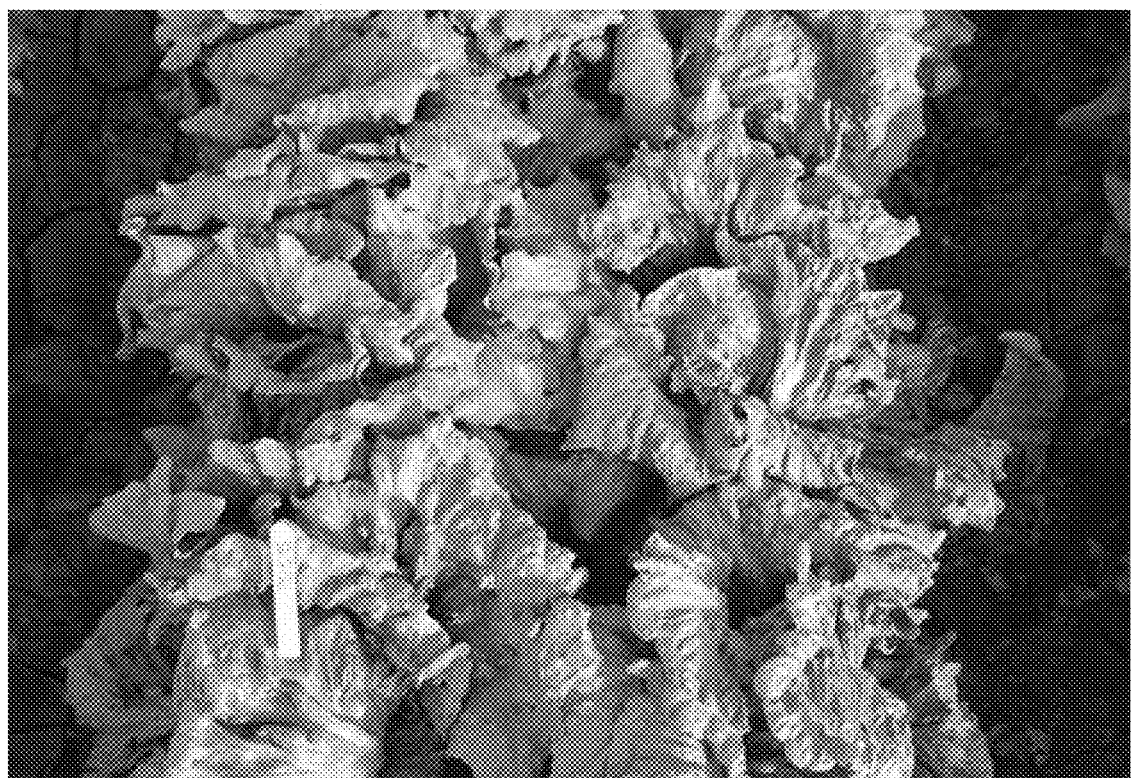
Figure 7G:
Figure 7H:
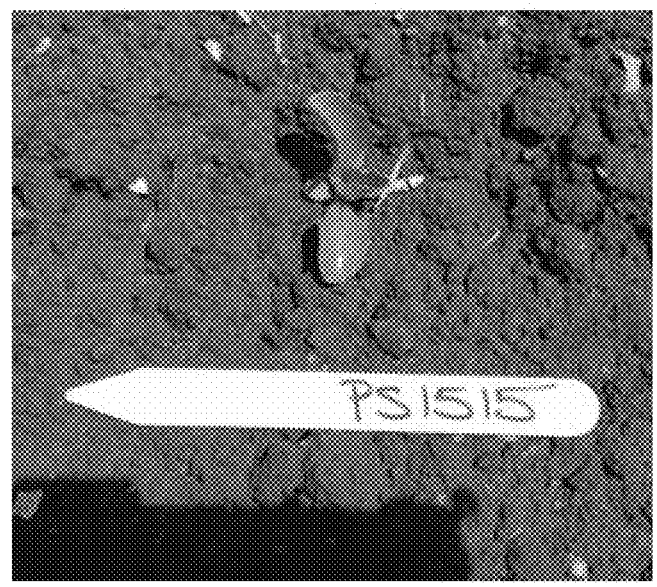
Figure 71:
Figure 7J:
Figure 8A:
FIGS. 8A-8M show a comparison between lettuce varieties 'Payday' (PS1515) and 'Primetime' (PS1037).
Figure 8B:
Figure 8C:
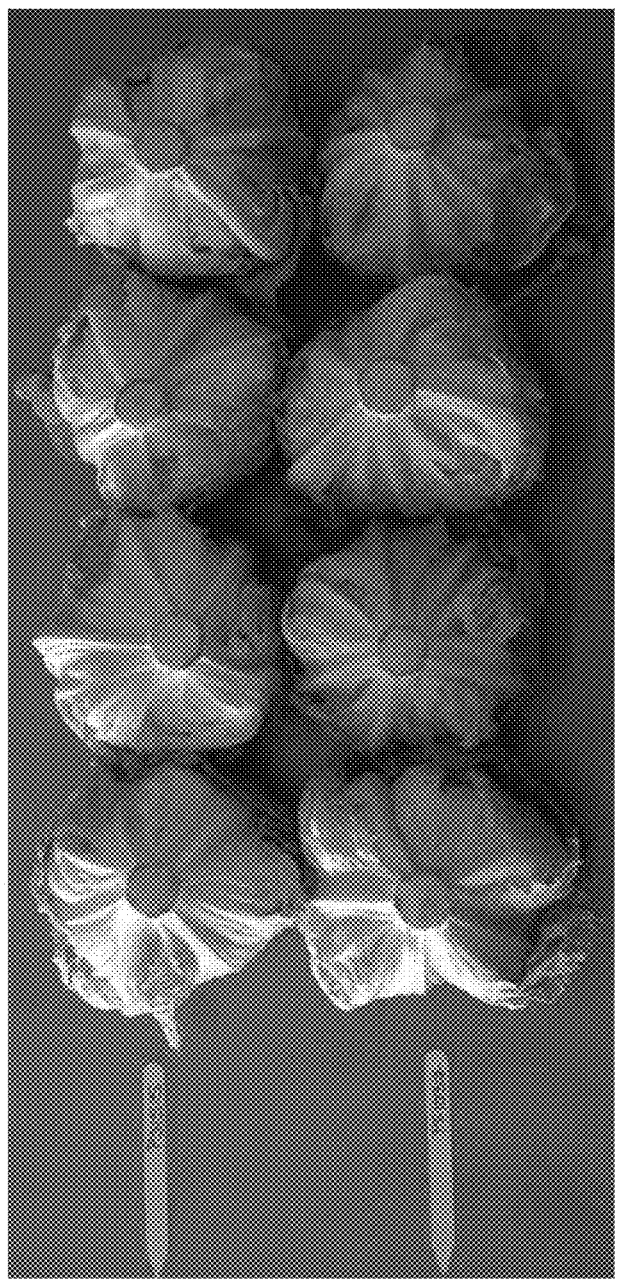
Figure 8D:
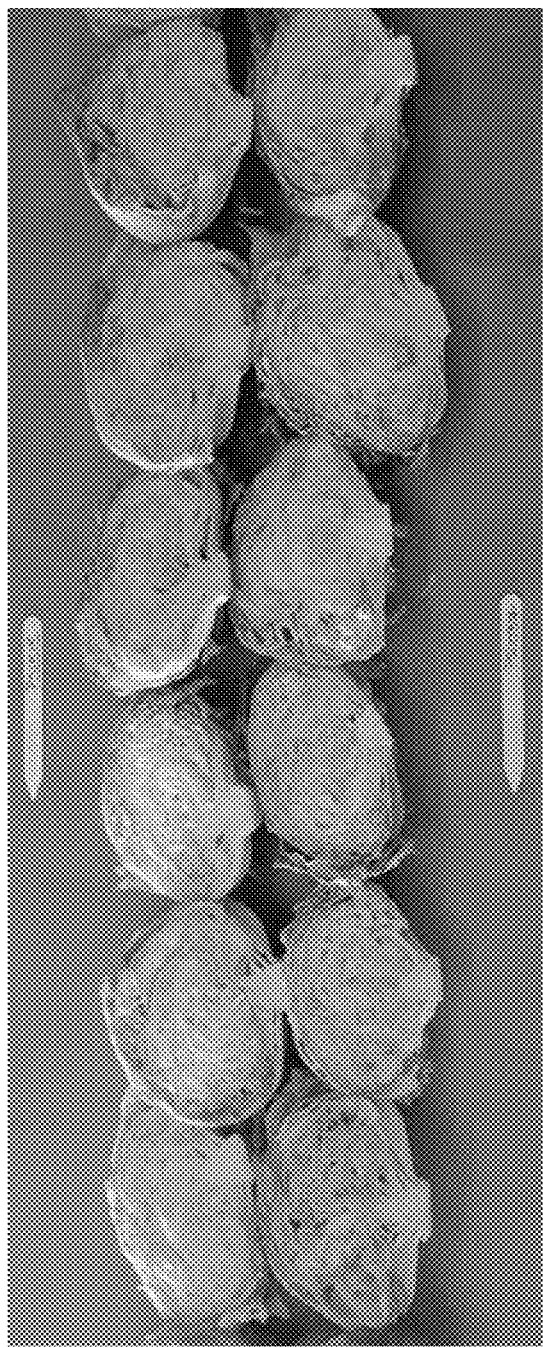
Figure 8E:
Figure 8F:
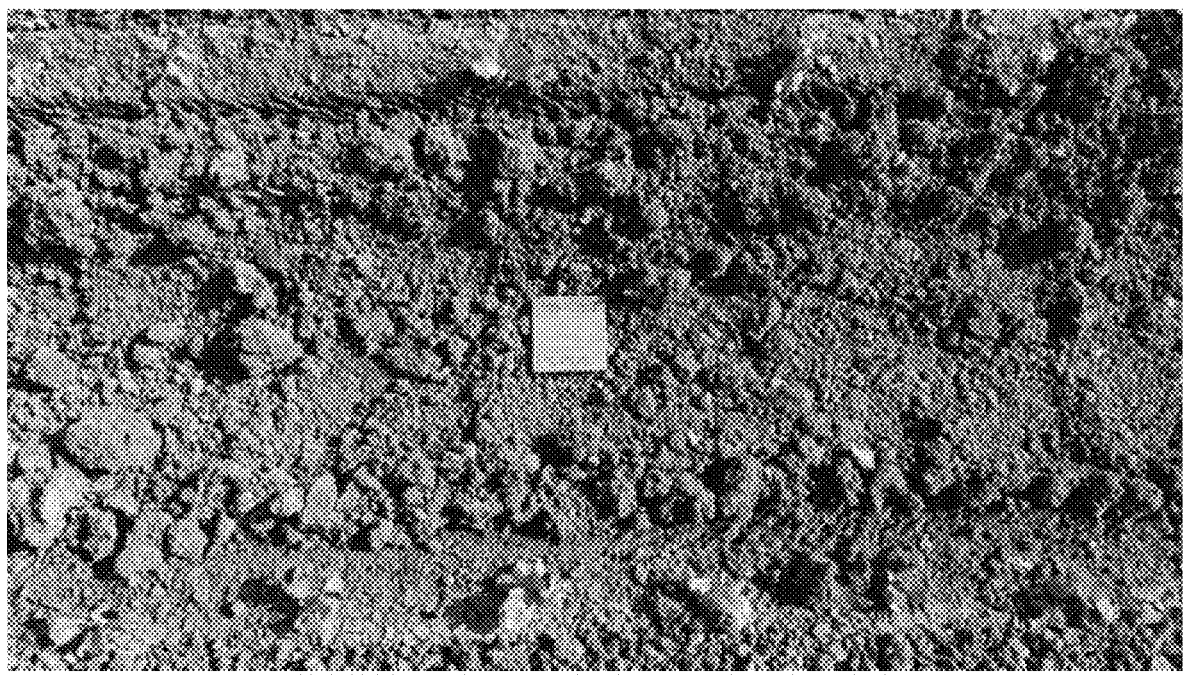
Figure 8G:
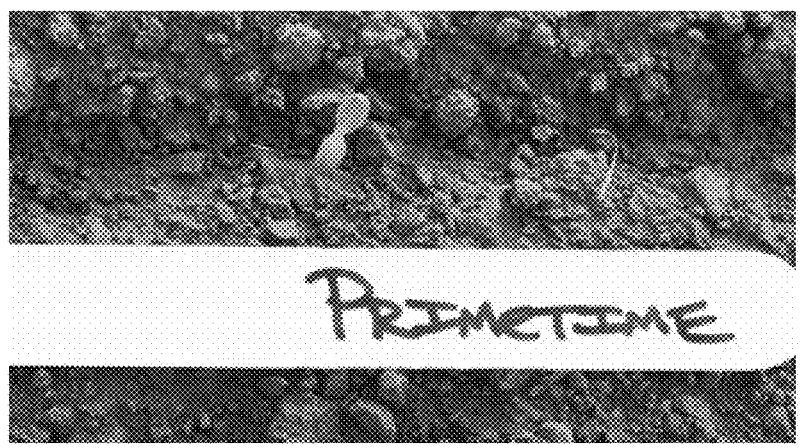
Figure 8H:
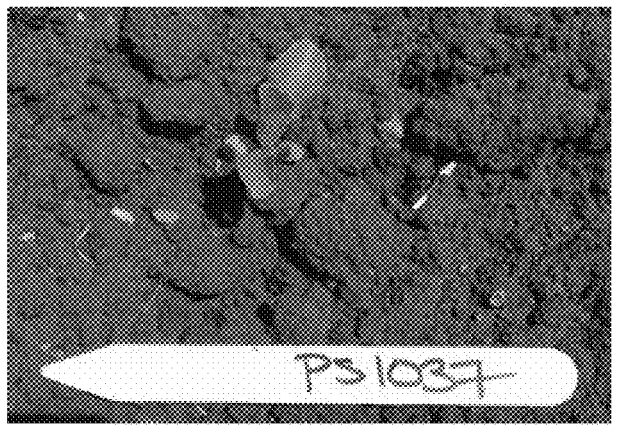
Figure 8I:
Figure 8J:
Figure 8K:
Figure 8L:
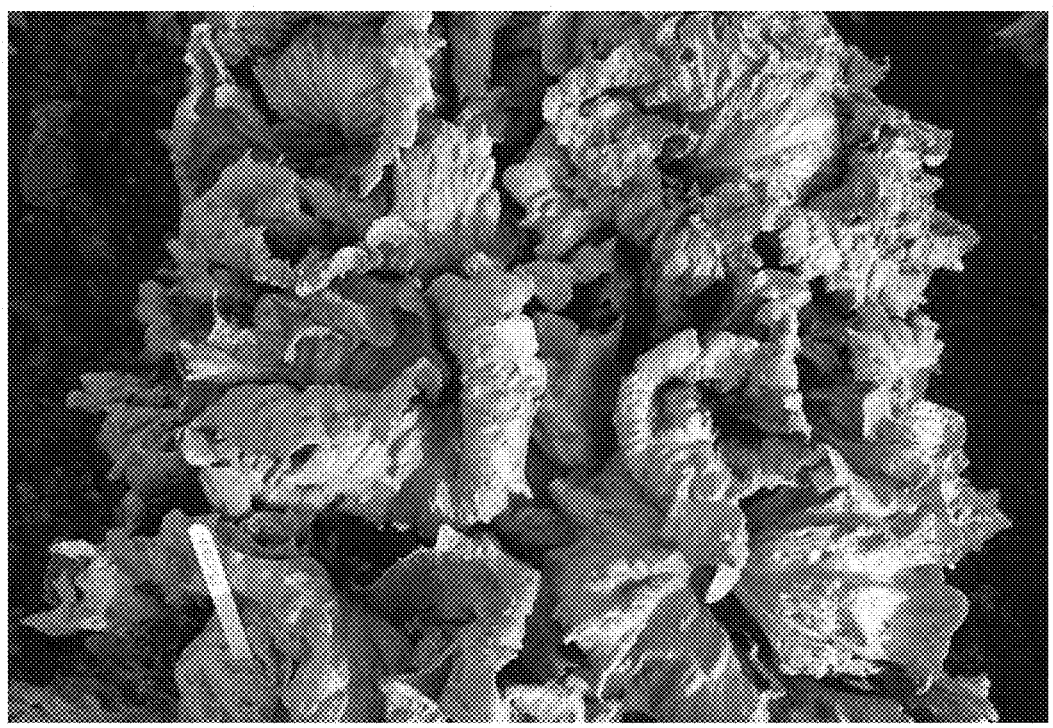
Figure 8M:

'Payday' is an open-pollinated iceberg lettuce variety. This variety is distinct and unique to all other iceberg lettuce varieties due to its improved weight, improved uniformity, larger frame, increased core diameter, increased core length, smaller head size, and earlier flowering. Moreover, 'Payday' has a growing season that includes autumn, and is suitable for cultivation in the open. 'Payday' is adapted to growing in regions such as the Southwest regions of the United States, for example California and the Arizona desert. FIGS. 7A-7D, 7F and 7I depict heads of lettuce variety 'Payday', FIGS. 7G-7H depict seedlings of lettuce variety 'Payday', FIG. 7E depicts plants of lettuce variety 'Payday', and FIG. 7J depicts bolting plants of lettuce variety 'Payday'. Lettuce variety 'Payday' is the result of numerous generations of plant selections chosen for its improved weight, improved uniformity, and larger frame.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Payday'.

Lettuce variety 'Payday' has the following morphologic and other characteristics:

Plant type: Crisp (i.e., iceberg); Vanguard Group
Seed:
Color: Black
Leaves:
Cotyledon to fourth leaf stage:
   Shape of cotyledons: Intermediate
   Shape of fourth leaf: Oval
   Apical margin: Moderately dentate
   Basal margin: Finely dentate
   Undulation: Medium
   Green color: Medium green
   Anthocyanin:
      Distribution: Absent
      Cupping: Slight
      Reflexing: None
Mature leaves:
   Incision depth of margin: Moderate (comparable to 'Vanguard')
   Indentation of margin: Crenate (comparable to 'Vanguard')
   Undulations of the apical margin: Moderate (comparable to 'Vanguard')
   Green color: Munsell 5GY 5/6 (Dark green; comparable to 'Vanguard')
   Hue of green color of mature outer leaves: Greyish
   Intensity of color of outer leaves: Medium
   Anthocyanin:
      Coloration: Absent
      Distribution: Absent
      Size: Medium
      Glossiness: Dull (comparable to 'Vanguard')
      Blistering: Moderate (comparable to 'Vanguard')
      Leaf thickness: Intermediate
      Trichomes: Absent (smooth)
Plant:
Spread of frame leaves: 44.6 cm
Head diameter: 138.9 mm
Head shape: Slightly flattened
Head degree of overlapping of upper part of leaves: Medium
Head size class: Medium
Head per carton: 24
Head weight: 602 g
Head firmness: Firm
Plant Butt:
Shape: Flat
Midrib: Moderately raised
Plant Core:
Diameter at base of head: 29.1 mm
Ratio of head diameter/core diameter: 4.7
Core height from base of head to apex: 33.6 mm Bolting:
Class: Medium
Bolter leaves: Curved
Margin: Entire
Color: Medium green
Days from first water date to seed stalk emergence under summer conditions: 73 days
Bolter Habit:
Lateral shoots: Absent
Basal side shoots: Present
Disease/Pest Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
Pests:
  *Nasonovia ribisnigri* biotype 0 (Nr:0): Susceptible
Comparisons to Other Lettuce Variety Table 15 below compares characteristics of lettuce variety 'Payday' with the lettuce variety 'Primetime' (PS1037). Column 1 lists the characteristics, column 2 shows the characteristics for lettuce variety 'Payday', and column 3 shows the characteristics for lettuce variety 'Primetime'.

TABLE 15

| Characteristic | 'Payday' | 'Primetime' |
| --- | --- | --- |
| Weight | Increased weight | Lower weight |
| Uniformity | Improved uniformity | Uniform |

TABLE 15-continued

| Characteristic | 'Payday' | 'Primetime' |
| --- | --- | --- |
| Frame | Larger frame | Smaller frame |
| Flowering time | Earlier flowering | Later flowering |
| Core diameter | Larger core diameter | Smaller core diameter |
| Stem length | Larger stem length | Smaller stem length |
| Head diameter | Smaller head diameter | Larger head diameter |

Table 16 below compares characteristics of lettuce variety 'Payday' with the lettuce variety 'Primetime'. Column 1 lists the characteristics, column 2 shows the characteristics for lettuce variety 'Payday', and column 3 shows the characteristics for lettuce variety 'Primetime'.

TABLE 16

| Characteristic | 'Payday' | 'Primetime' |
| --- | --- | --- |
| Green color of mature leaves | Munsell 5GY 5/6 | Munsell 5GY 6/6 |
| Spread of frame leaves | 44.6 cm | 43.9 cm |
| Head diameter | 138.9 mm | 139.4 mm |
| Head weight | 602 g | 547.1 g |
| Diameter at base of head | 29.1 mm | 28.6 mm |
| Core height from base to apex | 33.6 mm | 32.1 mm |

Tables 17A and 17B below show results of a first trial that compares the head weight, head diameter, core length, core diameter, and frame diameter of 20 plants of the lettuce variety 'Payday' (Table 17A) with those of 20 plants of lettuce variety 'Primetime' (Table 17B).

TABLE 17A

| 'Payday' | Head Wt. | Head Diameter | Core Length | Core Diameter | Frame Diameter |
| --- | --- | --- | --- | --- | --- |
| Max | 690 g | 161 mm | 42 mm | 33 mm | 49 cm |
| Min | 300 g | 121 mm | 27 mm | 27 mm | 42 cm |
| Average | 531.75 g | 141.25 mm | 33.55 mm | 29.75 mm | 45.5 cm |
| Std. Dev | 102.56 | 9.82 | 4.75 | 1.74 | 2.24 |

TABLE 17B

| 'Primetime' | Head Wt. | Head Diameter | Core Length | Core Diameter | Frame Diameter |
| --- | --- | --- | --- | --- | --- |
| Max | 755 g | 173 mm | 40 mm | 33 mm | 48 cm |
| Min | 355 g | 135 mm | 22 mm | 25 mm | 41 cm |
| Average | 483.68 g | 148.53 mm | 30.79 mm | 29.32 mm | 45.05 cm |
| Std. Dev | 122.82 | 10.07 | 5.58 | 2.38 | 2.27 |

Tables 18A and 18B below show results of a second trial that compares the head weight, head diameter, core length, core diameter, and frame diameter of 20 plants of the lettuce variety 'Payday' (Table 18A) with those of 20 plants of lettuce variety 'Primetime' (Table 18B).

TABLE 18A

| 'Payday' | Head Wt. | Head Diameter | Core Length | Core Diameter | Frame Diameter |
| --- | --- | --- | --- | --- | --- |
| Max | 790 g | 149 mm | 32 mm | 36 mm | 50 cm |
| Min | 485 g | 121 mm | 19 mm | 23 mm | 37 cm |
| Average | 645 g | 137.1 mm | 27.75 mm | 31 mm | 46.15 cm |
| Std. Dev | 92.02 | 7.50 | 3.48 | 3.23 | 3.05 |

TABLE 18B

| 'Primetime' | Head Wt. | Head Diameter | Core Length | Core Diameter | Frame Diameter |
|---|---|---|---|---|---|
| Max | 805 g | 147 mm | 34 mm | 34 mm | 50 cm |
| Min | 435 g | 119 mm | 22 mm | 27 mm | 42 cm |
| Average | 598.25 g | 133.15 mm | 27.95 mm | 31.55 mm | 45.85 cm |
| Std. Dev | 119.26 | 8.85 | 3.59 | 1.93 | 2.35 |

Tables 19A and 19B below show results of a third trial that compares the head weight, head diameter, core length, core diameter, and frame diameter of 20 plants of the lettuce variety 'Payday' (Table 19A) with those of 20 plants of lettuce variety 'Primetime' (Table 19B).

TABLE 19A

| 'Payday' | Head Wt. | Head Diameter | Core Length | Core Diameter | Frame Diameter |
|---|---|---|---|---|---|
| Max | 680 g | 160 mm | 50 mm | 32 mm | 47 cm |
| Min | 580 g | 121 mm | 27 mm | 23 mm | 36 cm |
| Average | 629.25 g | 138.45 mm | 39.6 mm | 26.65 mm | 42.05 cm |
| Std. Dev | 24.88 | 10.12 | 8.00 | 2.58 | 2.93 |

TABLE 19B

| 'Primetime' | Head Wt. | Head Diameter | Core Length | Core Diameter | Frame Diameter |
|---|---|---|---|---|---|
| Max | 640 g | 160 mm | 51 mm | 29 mm | 48 cm |
| Min | 480 g | 115 mm | 25 mm | 22 mm | 34 cm |
| Average | 559.25 g | 136.65 mm | 37.55 mm | 25 mm | 41.05 cm |
| Std. Dev | 47.99 | 12.40 | 7.74 | 1.62 | 3.61 |

Further distinguishing features are apparent from the comparison of the two varieties depicted in FIGS. 8A-8M.

Further Embodiments

Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Ariz. and the Salinas Valley, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

Lettuce Variety 'Payday'

A deposit of the lettuce variety 'Payday' is maintained by Pinnacle Seed, Inc., having an address of P.O. Box 222672, Carmel, Calif. 93923, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

The lettuce variety 'Payday' was deposited on Dec. 13, 2021 according to the Budapest Treaty in the American Type Culture Collection (ATCC), ATCC Patent Depository, 10801 University Boulevard, Manassas, Va., 20110, USA. The deposit has been assigned ATCC Number PTA-127190. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed:

1. A *Lactuca sativa* seed designated as 'Payday', representative sample of seed having been deposited under ATCC Accession Number PTA-127190.

2. A *Lactuca sativa* plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a leaf, or a portion thereof.

9. The plant part of claim 8, wherein said part is a head.

10. An F1 hybrid *Lactuca sativa* plant having 'Payday' as a parent where 'Payday' is grown from the seed of claim 1.

11. A pollen grain or an ovule of the plant of claim 2.

12. A tissue culture of the plant of claim 2.

13. A *Lactuca sativa* plant regenerated from the tissue culture of claim 12, wherein the plant has all of the morphological and physiological characteristics of a lettuce plant produced by growing seed designated as 'Payday', representative sample of seed having been deposited under ATCC Accession Number PTA-127190.

14. A method of making *Lactuca sativa* seeds, said method comprising crossing the plant of claim 2 with another lettuce plant and harvesting seed therefrom.

15. A method of selecting *Lactuca sativa*, comprising:
   a) growing more than one plant from the seed of claim 1; and
   b) selecting a plant from step a) with improved weight, improved uniformity, and larger frame.

16. A *Lactuca sativa* plant selected by the method of claim 15.

17. A *Lactuca sativa* seed produced from the *Lactuca sativa* plant of claim 16.

* * * * *